(12) United States Patent
Linden et al.

(10) Patent No.: US 6,670,334 B2
(45) Date of Patent: Dec. 30, 2003

(54) METHOD AND COMPOSITIONS FOR TREATING THE INFLAMMATORY RESPONSE

(75) Inventors: Joel M. Linden, Charlottesville, VA (US); Jayson M. Rieger, Charlottesville, VA (US); Gail W. Sullivan, Charlottesville, VA (US); Timothy L. Macdonald, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 0 days.

(21) Appl. No.: 10/041,776

(22) Filed: Jan. 7, 2002

(65) Prior Publication Data

US 2002/0111327 A1 Aug. 15, 2002

Related U.S. Application Data

(60) Provisional application No. 60/260,059, filed on Jan. 5, 2001.

(51) Int. Cl.[7] ............................................. A61K 31/70
(52) U.S. Cl. ........................... 514/46; 514/44; 514/49; 435/91.2; 435/6; 536/22.1
(58) Field of Search ............................ 514/46, 49, 44; 536/22.1; 435/91.2, 6

(56) References Cited

U.S. PATENT DOCUMENTS

| | | | |
|---|---|---|---|
| 4,193,926 A | 3/1980 | Schmiechen et al. | 260/326.5 |
| 4,242,345 A | 12/1980 | Brenner et al. | 424/253 |
| 4,824,660 A | 4/1989 | Angello et al. | 424/1.1 |
| 4,879,296 A | 11/1989 | Daluge et al. | 514/263 |
| 4,956,345 A | 9/1990 | Miyasaka et al. | 514/46 |
| 4,968,697 A | 11/1990 | Hutchison | 514/46 |
| 5,096,906 A | 3/1992 | Mandell et al. | 514/263 |
| 5,140,015 A | 8/1992 | Olsson et al. | 514/46 |
| 5,189,027 A | 2/1993 | Miyashita et al. | 514/46 |
| 5,272,153 A | 12/1993 | Mandell et al. | 514/263 |
| 5,278,150 A | 1/1994 | Olsson et al. | 514/46 |
| 5,298,508 A | 3/1994 | Jacobson et al. | 514/263 |
| 5,364,862 A | 11/1994 | Spada et al. | 514/303 |
| 5,561,134 A | 10/1996 | Spada et al. | 514/266 |
| 5,565,462 A | 10/1996 | Eitan et al. | 514/262 |
| 5,593,975 A | 1/1997 | Cristalli | 514/46 |
| 5,665,754 A | 9/1997 | Feldman et al. | 514/397 |
| 5,668,139 A | 9/1997 | Belardinelli et al. | 514/263 |
| 5,776,940 A | 7/1998 | Daluge et al. | 514/263 |
| 5,877,180 A | 3/1999 | Linden et al. | 514/266 |
| 5,932,558 A | 8/1999 | Cronstein et al. | 514/46 |
| 5,998,386 A | 12/1999 | Feldman | 514/46 |
| 6,004,945 A | 12/1999 | Fukunaga | 514/46 |
| RE36,494 E | 1/2000 | Olsson et al. | 514/46 |
| 6,020,321 A | 2/2000 | Cronstein et al. | 514/46 |
| 6,020,339 A | 2/2000 | Perrier et al. | 514/269 |
| 6,034,089 A | 3/2000 | Han et al. | 514/269 |
| 6,326,359 B1 | 12/2001 | Monaghan et al. | 514/46 |
| 6,339,072 B2 | 1/2002 | Martin et al. | 514/46 |
| 6,448,235 B1 * | 9/2002 | Linden et al. | 514/46 |

FOREIGN PATENT DOCUMENTS

| | | | |
|---|---|---|---|
| EP | 0700908 | 3/1996 | ......... C07D/239/54 |
| WO | WO-95/11681 | 5/1995 | .......... A61K/31/52 |
| WO | WO-9604280 | 2/1996 | ......... C07D/473/06 |
| WO | WO-98/57651 | 12/1998 | .......... A61K/31/70 |
| WO | WO-99/63938 | 12/1999 | |
| WO | WO-99/67264 | 12/1999 | ......... C07H/19/167 |
| WO | WO-00/78777 | 12/2000 | ........... C07H/19/16 |

OTHER PUBLICATIONS

Abiru, T.,et al. ,"Nucleosides and Nucleotides. 107. 2–(Cycloalkylalkynyl)adenosines: Adenosine A2 Receptor Agonists with Potent Antihypertensive Effects", *Journal of Medicinal Chemistry, 35,* (1992),pp. 2253–2260.

Ali, H.,et al. ,"Methylxanthines Block Antigen–induced Responses in RBL–2H3 Cells Independently of Adenosine Receptors or Cyclic AMP: Evidence for Inhibition of Antigen Binding to IgE", *Journal of Pharmacology and Experimental Therapeutics, 258,* (1991),pp. 954–962.

Andersson, P.,et al. ,"Anti–anaphylactic and anti–inflammatory effects of xanthines in the lung", *Curr. Clin. Pract. Ser.,* (1985),pp. 187–192.

Bridges, A.J. ,"N6–[2–(3, 5–Dimethoxyphenyl)–2–(2–Methylphenyl)–Ethyl]Adenosine and Its Uronamide Derivatives. Novel Adenosine Agonists With Both High Affinity and High Selectivity for the Adenosine A2 Receptor", *Journal of Medicinal Chemistry, 31 (7),* (1988),pp. 1282–1285.

Bruns, R.F. ,et al. ,"Characterization of the A2 Adenosine Receptor Labeled by [3H]NECA in Rat Striatal Membranes", *Molecular Pharmacology, 29,* (1986),pp. 331–346.

Buster, B.,et al. ,"The Effect of Adenosine Receptor Agonists on Neutrophil Pleocytosis and Blood–Brain Barrier Pathophysiology in Experimental Bacterial Meningitis", *Abstract of the Interscience Conference on Antibmicrobial Agents and Chemotherapy, 37,* Abstract No. B–72,(1997),p. 39.

Cembrzynska–Nowak, M.,et al. ,"Elevated Release of Tumor Necrosis Factor–alpha and Interferon–gamma by Bronchoalveolar Leukocytes From Patients With Bronchial Asthma.", *American Review of Respiratory Disease, 147(2),* (1993),291–295.

Cristalli, G.,"2–Alkynyl Derivatives of Adenosine an Adenosine–5'–N–ethyluronamide as Selective Agonists at A2 Adenosine Receptors", *Journal of Medicinal Chemistry, 35 (13),* (1992),pp. 2363–2368.

(List continued on next page.)

*Primary Examiner*—James O. Wilson
*Assistant Examiner*—LaTonia M. Fisher
(74) *Attorney, Agent, or Firm*—Schwegman, Lundberg, Woessner & Kluth, P.A.

(57) ABSTRACT

Agonists of $A_{2A}$ adenosine receptors optionally, in combination with a Type IV phosphodiesterase (PDE) inhibitor are effective for the inhibition of an inflammatory response in mammalian tissue, in vivo or in vitro.

21 Claims, 11 Drawing Sheets

OTHER PUBLICATIONS

Cronstein, B.N. ,"Adenosine Modulates the Generation of Superoxide Anion by Stimulated Human Neutrophils Via Interaction With a Specific Cell Surface Receptor", *Annals New York Academy of Science, 451*, (1985),291–314.

Cronstein, B.N. ,"Adenosine; A Physiologic Modulator Of Superoxide Anion Generated By Human Neutrophils. Adenosine Acts Via An A2 Receptor On Human Neutrophils", *Journal Of Immunology, 135*(2), (1985),pp. 1366–1371.

Cronstein, B.N. ,"Engagement of Adenosine Receptors Inhibits Hydrogen Peroxide (H2O2) Release by Activated Human Neutrophils", *Clinical Immunology and Immunopathology, 42*(1), (1987),76–85.

Cronstein, B.N. ,"Methotrexate Inhibits Leukocyte Influx Into Inflammatory Sites Via The Adenosine (A2) Receptor", *Clinical Research, 41* (2), (1993),p. 244A.

Cronstein, B.N.,et al. ,"Neutrophil Adherence to Endothelium is Enhanced Via Adenosine A1 Receptors and Inhibited Via Adenosine A2 Receptors", *The Journal of Immunology, 148* (7), (1992),pp. 2201–2206.

Cronstein, N.,et al. ,"Occupancy Of Adenosine Receptors Raises Cyclic AMP Alone And In Synergy With Occupancy Of Chemoattractant Receptors And Inhibits Membrane Depolarization", *Biochemical Journal, 252* (3), (1988),pp. 709–715.

Cronstein, B.N. ,"The Adenosine/Neutrophil Paradox Resolved: Human Neutrophils Possess Both A1 and A2 Receptors That Promote Chemotaxis and Inhibits O2 Generation, Respectively", *Journal of Clinical Investigation, 85* (4), (1990),pp. 1150–1157.

De La Harpe, J.,"Adenosine Regulates the Respiratory Burst Of Cytokine—Triggered Human Neutrophils Adherent To Biological Surfaces", *Journal Of Immunology, 143*(2), (1989),596–602.

Dinarello, C.A. ,"Interleukin–1 And Tumor Necrosis Factor: Effector Cytokines In Autoimmune Diseases", *Seminars in Immunology, 4*, (1992),133–145.

Doyl, M.P. ,et al. ,"Nucleoside–induced Arteriolar Constriction: a Mast Cell–dependent Response.", *American Journal of Physiology*, (May 1994),pp. H2042–H2050.

Fang, G.D. ,et al. ,"A New Selective Adenosine A2a Receptor Agonist, Improves Survival in *E. coli* O26:B6 Lipopolysaccharide (LPS)–Induced Experimental Murine Endotoxemia", *Journal of Investigative Medicine*, Abstract No. 797,(2000),p. 148A.

Feoktistov, I.,et al. ,"Adenosine A2b receptors", *The American Society for Pharmacological and Experimental Therapeutics, 49* (4), (1997),pp. 381–402.

Firestein, G.S. ,"Adenosine Regulating Agents: A Novel Approach to Inflammation and Inflammatory Arthritis", *Clinical Research, 41*(2), (1993),170A.

Fozard, J.R. ,"Adenosine A3 Receptors Mediate Hypotension in the Angiotensin II–supported Circulation of the Pithed Rat", *British Journal of Pharmacology, 109* (1), (1993),pp. 3–5.

Francis, J.E. ,"Highly Selective Adenosine A2 Receptor Agonists in a Series of N–Alkylated 2–Aminoadenosines", *Journal of Medicinal Chemistry, 34* (8), (1991),pp. 2570–2579.

Glover, D.K. ,et al. ,"Pharmacological Stress Thallium Scintigraphy With 2–Cyclohexylmethylidenehydrazinoadenosine (WRC–0470) A Novel, Short–Acting Adenosine A2A Receptor Agonist.", *Circulation, 94*, (1996),pp. 1726–1732.

Griswold, D.E. ,et al. ,"Effects of Selective Phosphodiesterase Type IV Inhibitor, Rolipram, on Fluid and Cellular Phases of Inflammatory Response", *Chemical Abstracts, 119*, Abstract No. 173828e,(1993),p. 49.

Hanlon, W.A. ,"rTNF alpha Facilitate Human Polymorphonuclear Leukocyte Adherence to Fibrinogen Matrices With Mobilization of Specific and Tertiary But Not Azurophilic Granule Markers", *Journal of Leukocyte Biology, 50 (1)*, (1991),pp. 43–48.

Hartung, H.P. ,"Immune–Mediated Demyelination", *Annals of Neurology, 33* (6), (Jun. 1993),pp. 563–567.

Holmes,"Restenosis After Percutaneous Transluminal Coronary Angioplasty (PTCA): A Report From the PTCA Registry of the National Heart, Lung, and Blood Institute", *American Journal of Cardiology, 53*, (1984),77C–81C.

Hussain, T.,et al. ,"1251–APE Binding to Adenosine Receptors in Coronary Artery: Photoaffinity Labeling With 1251–azidoAPE", *The Journal of Pharmacology and Experimental Therapeutics, 276 (1)*, (Jan. 1996),pp. 284–288.

Hutchison, A.J. ,"2–(Arylalkylamino)Adenosine–5'–Uronamides: A New Class of Highly Selective Adenosine A2 Receptor Ligands", *Journal of Medicinal Chemistry, 33* (7), (1990),pp. 1919–1924.

Hutchison, A.J. ,"CGS 21680C, an A2 Selective Adenosine Receptor Agonist With Preferential Hypotensive Activity", *The Journal of Pharmacology and Experimental Therapeutics, 251 (1)*, (1989),pp. 47–55.

Iannone, M.A. ,"Effects of Adenosine on Human Neutrophil Function and Cyclic AMP Content", *In: Topics and Perspectives in Adenosine Research*, Eds. E. Gerlach et al., Springer–Verlag, Berlin, Germany,(1986),pp. 286–298.

Imagawa, D.K. ,et al. ,"The Role of Tumor Necrosis Factor in Allograft Rejection", *Transplantation, 51*, (Jan. 1991), 57–62.

Jarvis, M.F. ,"[3H]CGS 21680, A Selective A2 Adenosine Receptor Agonist Directly Labels A2 Receptors in Rat Brain.", *Journal of Pharmacology and Experimental Therapeutics, 251*(3), (Dec. 1989),pp. 888–893.

Jolly, S.R. ,et al. ,"Effects of Lodoxarnide on Ischemic Reperfused Myocardium", *Journal of Cardiovascular Pharmacology, 4* (3), (1982),pp. 441–448.

Kaminuma, et al. ,"Effect of T–440, a Novel Type IV Phosphodiesterase Inhibitor, on Allergen–Induced Immediate and Late Asthmatic Reaction and Leukocyte Infiltration into the Airways of Guinea Pigs", *International Archives of Allergy & Immunology, 112*(4), (1997),406–411.

Kennedy, A.P. ,et al. ,"Covalent Modification of Transmembrane Span III of the A1 Adenosine Receptor With an antagonist Photoaffinity Probe.", *Molecular Pharmacology, 50*, (Oct. 1996),pp. 789–798.

Koshiba, M.,"Patterns of A2A Extracellular Adenosine Receptor Expression in Different Functional Subsets of Human Peripheral T Cells", *The FASEB Journal, Abstract No. 703.38*, (1999),p. A944.

Legrand–Poels, S.,"Activation of Human Immunodeficiency Virus Type 1 by Oxidative Stress", *AIDS Research and Human Retroviruses, 6*(12), (1990),1389–1397.

Linden, J.,et al. ,"(125I)Aminobenzyladenosine, a New Radioligand with Improved Specific Binding to Adenosine Receptors in Heart", Circulation Research, 56 (2), (Feb. 1985),pp. 279–284.

Luthin, D.R. ,et al. ,"Adenosine Receptors",Biomembranes, 2B, (1996),pp. 321–347.

Luthin, D.R. ,et al. ,"Characterization of Two Affinity States of Adenosine A2a Receptors With a New Radioligand, 2–[2–(4–amino–3–[125I]iodophenyl) Ethylamino]Adenosine.", Molecular Pharmacology, 47 (2), (Feb. 1995),pp. 307–313.

Luthin, D.R. ,et al. ,"Comparison of A4 and A2a Binding Sites in Striatum and COS Cells Transfected With Adesosine A2a Receptors.", The Journal of Pharmacology and Experimental Therapeutics, 272, (Feb. 1995),pp. 511–518.

Luthin, D.R. ,et al. ,"Photoaffinity Labeling With 2(-) [2–(4–azido–3(-)[125I]–iodophenyl)ethylamino]Adenosine and Autoradiography With 2(-)[2–(4–amino–3(-)[125I] iodophenyl)ethylamino]Adenosine of A2a Adenosine Receptor in Rat Brain.", Journal of Neurochemistry, 65 (5), (Nov. 1995),pp. 2072–2079.

Mager, P. ,"Neutal network approaches applied to selective A2a adenosine receptor agonists", Med. Chem. Res., vol. 8, No. 6, (1998),pp. 277–290.

Mannel, D.N. ,"Tumor Necrosis Factor: A Cytokine Involved in Toxic Effects of Endotoxin", Reviews of Infectious Diseases, 9, (1987),S602–S606.

Martin, P.L. ,et al. ,"Characterization of 8–(N–methylisopropyl)amino–N6–(5'–andohydroxy–endonorbornyl)9–methyladenine (WRC–0571), a Highly Potent and Selective, Non–xanthine Antagonist of A1 Adenosine Receptors.", The Journal of Pharmacology and Experimental Therapeutics, 276 (2), (Feb. 1996),pp. 490–499.

Martin, P.L. ,et al. ,"Pharmacology of 2–cyclohexylmethylidenehydrazinoadenosine (WRC–0470), a Novel, Short-acting Adenosine A2A Receptor Agonist That Produces Selective Coronary Vasodilation.", Drug Development Research, 40 (4), (1997),pp. 313–324.

Matsuyama, T.,"Cytokines and HIV Inection: is AIDS a Tumor Necrosis Factor Disease?", AIDS, 5(12), (1991), 1405–1417.

McGarrity, S.T. ,"Inhibition of Neutrophil Superoxide Anion Generation by Platelet Products: Role of Adenine Nucleotides", Journal of Leukocyte Biology, 44(5), (1988),411–421.

McGarrity, S.T. ,"Regulation of Human Neutrophil Function by Adenine Nucleotides", Journal of Immunololgy, 142(6), (1989),1986–1994.

McPherson, J.A. ,et al. ,"Effect of Prolonged Adenosine A2A Receptor Activation on Neointimal Formation in the Injured Mouse Carotid Artery", The FASEB Journal, Abstract No. 299.2, (1999),p. A367.

Molnar–Kimber, K.L. ,et al. ,"Modulation of TNF alpha and IL–1 beta From Endotoxin–Stimulated Monocytes by Selective PDE Isozyme Inhibitors", Agents & Actions, 39, (1993), C77–C79.

Nielson, C.P. ,"Effects of Adenosine on Polymorphonuclaer Leucocyte Function, Cyclic 3': 5'–adenosine Monophosphate, and Intracellular Calcium", British Journal of Pharmacology, 97(3), (1989),882–888.

Niiya, K.,"2–(N'–Alkylidenehydrazino)Adenosines: Potent and Selective Coronary Vasodilators", Journal of Medicinal Chemistry, 35 (24), (1992),pp. 4557–4561.

Nolte,"Reduction of Postischemic Leukocyte–Endothelium Interaction by Adenosine Via A2 Receptor", Biological Abstract, 94 (11), Abstract No. 116779,(1992),1 page.

O'Regan, M.H. ,et al. ,"Adenosine Receptor Agonists Inhibit the Release of y–Aminobutyric Acid (GABA) From the Ischemic Rat Cerebral Cortex", Chemical Abstracts, 117, Abstract No. 104867p,(1992),p. 170.

Okusa, Mark.D. ,"Selective A2A adenosine receptor activation reduces ischemia–referfusion injury in rat kidney", Am. J. Physiol., 3 (Pt 2), (1999),pp. F404–F412.

Olsson, R.A. ,"N6 Substituted N–Alkyladenosine–5'–Uronamides: Bifunctional Ligands Having Recognition Groups for A1 and A2 Adenosine Receptors", Journal of Medicinal Chemistry, 29 (9), (1986), pp. 1683–1689.

Peet, N.P. ,"Conformationally Restrained, Chiral (Phenylisopropyl)Amino–Substituted Pyrazolo[3,4–d]Pyrimidines and Purines With Selectivity for Adenosine A1 and A2 Receptors", Journal of Medicinal Chemistry, 35 (17), (1992),pp. 3263–3269.

Pfister, J.R. ,et al. ,"Synthesis and Biological Evaluation of the Enantiomers of the Potent and Seletive A1—adenosine Antagonist 1,3–dipropyl–8–[2–(5,6–epoxynorbonyl)]–xanthine", Journal of Medicinal Chemistry, 40 (12), (Jun. 1997),pp. 1773–1778.

Pulle, V.,et al. ,"Design, Synthesis And Pharmacological Evaluation Of 2(1–Alkyl–Pyrazol–4–YL) Adenosine Derivatives As Short Acting Adenosine A2A Receptor Agonists", Drug Development Research, 50 (1), Abstracts From Purines 2000: Biochemical, Pharmacological and Clinical Perspectives: Abstract No. 062,(May 2000),p. 64.

Roberts, P.A. ,"Inhibition by Adenosine of Reactive Oxygen Metabolite Production by Human Polymorphonuclear Leucocytes", Biochemical Journal, 227(2), (1985),669–674.

Sawmiller, D.R. ,et al. ,"Effects of Xanthine Amine Congener on Hypoxic Resistance and Venous and Epicardial Adenosine Concentrations.", Cardiovascular Research, 28 (5), (May 1994),pp. 604–609.

Schlack,et al. ,"Adenosine A2–Receptor Activation at Reperfusion reduces Infarct Size and Improves Myocardial Wall Function in Dog Heart", Biological Abstract, 96 (6), Abstract No. 67801,(1993),1 page.

Schrier, D.J. ,"The Effects of Adenosine Agonists on Human Neutrophil Function", Journal of Immunology, 137 (10), (1986),pp. 3284–3289.

Seekamp, A., "Ischemia—Reperfusion Injury", Agents and Actions Supplements, 41, (1993),137–152.

Sharief, M.K. ,et al. ,"Elevated Serum Levels of Tumor Necrosis Factor–alpha in Guillain–Barre Syndrome", Annals of Neurology, 33, (Jun. 1993),591–596.

Sipka, S.,"Adensoine Induced Delay of Expression of AIDS Virus, HIV, in H9T Cells", Acta. Biochimica et Biophysica Hungarica, 23(1), (1988),75–82.

Smits, Paul.,et al. ,"Cardiovascular effects of two xanthines and the relation to adenosine antagonism", Clinical Pharmacology and Therapeutics, 45 (6), (1989),pp. 593–599.

Sullivan, G.W. ,"Adenosine (ADO) Modulates Endotoxin and TNF–Induced PMN Activation", Clinical Research, 41(2), (1993),172A.

Sullivan, G.W., et al., "Role of A2A Adensoine Receptors in Inflammation", *Drug Development Research, 45* (3/4), (1998),pp. 103–112.

Sullivan, G.W., "The Specific Type IV Phosphodiesterase Inhibitor Rolipram Combined with Adenosine Reduces Tumor Necrosis Factor–a–Primed Neutrophil Oxidative Activity", *International Journal of Immunopharmacology, 17(10)*, (1995),793–803.

Sullivan, G.W., et al., "Two Methylxanthines, Pentoxifylline (PTX) and Caffeine (CAF) Have Divergent Effects on Tumor Necrosis Factor (TNF)–Primed Human Neutrophil (PMN) Activation", *Clinical Research, 41(2)*, (1993),p. 172A.

Tracey, K.J., "Cachectin/Tumor Necrosis Factor Induces Cachexia, Anemia, and Inflammation", *Journal of Experimental Medicine, 167*, (Mar. 1988),1211–1227.

Ueeda, M.,et al., "2–Alkoxyadenosines: Potent and Selective Agonists at the Coronary Artery A2 Adensoine Receptor", *J. Med. Chem., 34*, (1991),pp. 1334–1339.

Underwood, D.C., et al., "Inhibition of Antigen–Induced Bronchoconstriction and Eosinophil Infiltration in the Guinea by The Cyclic AMP–Specific Phosphodiesterase Inhibitor, Rolipram", *Chemical Absracts, 119 (16)*, Abstract No. 173975a,(1993),p. 67.

Van Calker, D.,et al., "Adenosine Regulates via Two Different Types of Receptors, the Accumulation of Cyclic Amp in Cultured Brain Cells", *Journal of Neurochemistry, 33*, (1979),pp. 999–1005.

Van Calker, D., "Carbamazepine Distinguishes Between Adenosine Receotors That Mediate Different Second Messenger Responses", *European Journal of Pharmacology, 206 (4)*, (1991),pp. 285–290.

Walker, B.,et al., "Adenosine A2a Receptor Activation Delays Apoptosis in Human Neutrophils", *The American Association of Immunologists*, (1997),pp. 2926–2931.

Wan, A.A., et al., "Binding of the Adenosine A2 Receptor Ligand (3H)CGS 21680 to Human and Rat Brain: Evidence for Multiple Affinity Sites", *Journal of Neurochemistry*, (1990),pp. 1763–1771.

Yoneyama, F., "Vasodepressor Mechanisms of 2–(1–octynyl) –Adenosine (YT–146), a Selective Adenosine A2 Receptor Agonist, Involve the Opening of Glibenclamide-sensitive K+ Channels", *European Journal of Pharmacology, 213 (1)*, (1992),pp. 199–204.

* cited by examiner

METHOD AND COMPOSITIONS FOR TREATING THE INFLAMMATORY RESPONSE

CROSS-REFERENCE TO RELATED APPLICATIONS

This application claims benefit under 35 U.S.C. 119(e) of U.S. Provisional Application Serial No. 60/260,059 filed Jan. 5, 2001.

STATEMENT OF GOVERNMENT RIGHTS

This invention was made with a grant from the Government of the United States of America (Grant RO1 HL37942 from the National Institute of Health). The Government may have certain rights in the invention.

BACKGROUND OF THE INVENTION

The release of inflammatory cytokines such as tumor necrosis factor-alpha (TNFα) by leukocytes is one means by which the immune system combats pathogenic invasions, including infections. Cytokines stimulate neutrophils to enhance oxidative (e.g., superoxide and secondary products) and nonoxidative (e.g., myeloperoxidase and other enzymes) inflammatory activity. Inappropriate and over-release of cytokines can produce counterproductive exaggerated pathogenic effects through the release of tissue-damaging oxidative and nonoxidative products (Tracey, K. G. et al., *J. Exp. Med.*, 167, 1211–1227 (1988); and Männel, D. N. et al., *Rev. Infect. Dis.*, 9 (suppl 5), S602–S606 (1987)).

For example, inflammatory cytokines have been shown to be pathogenic in: arthritis (Dinarello, C. A., *Semin. Immunol.*, 4, 133–45 (1992)); ischemia (Seekamp, A. et al., *Agents-Actions-Supp.*, 41, 137–52 (1993)); septic shock (Männel, D. N. et al., *Rev. Infect. Dis.*, 9 (suppl 5), S602–S606 (1987)); asthma (Cembrzynska Nowak M. et al., *Am. Rev. Respir. Dis.*, 147, 291–5 (1993)); organ transplant rejection (Imagawa, D. K. et al., *Transplantation*, 51, 57–62 (1991)); multiple sclerosis (Hartung, H. P., *Ann. Neurol.*, 33, 591–6 (1993)); and AIDS (Matsuyama, T. et al., *AIDS*, 5, 1405–1417 (1991)). In addition, superoxide formation in leukocytes has been implicated in promoting replication of the human immunodeficiency virus (HIV) (Legrand-Poels, S. et al., *AIDS Res. Hum. Retroviruses*, 6, 1389–1397 (1990)).

It is well known that adenosine and some adenosine analogs that non-selectively activate adenosine receptor subtypes decrease neutrophil production of inflammatory oxidative products (Cronstein, B. N. et al., *Ann. N.Y. Acad. Sci.*, 451, 291–314 (1985); Roberts, P. A. et al., *Biochem. J.*, 227, 669–674 (1985); Schrier, D. J. et al., *J. Immunol.*, 137, 3284–3289 (1986); Cronstein, B. N. et al., *Clinical Immunol. and Immunopath.*, 42, 76–85 (1987); Iannone, M. A. et al., in *Topics and Perspectives in Adenosine Research*, E. Gerlach et al., eds., Springer-Verlag, Berlin, 286–298 (1987); McGarrity, S. T. et al., *J. Leukocyte Biol.*, 44, 411–421 (1988); De La Harpe, J. et al., *J. Immunol.*, 143, 596–602 (1989); McGarrity, S. T. et al., *J. Immunol.*, 142, 1986–1994 (1989); and Nielson, C. P. et al., *Br. J. Pharmacol.*, 97, 882–888 (1989)). For example, adenosine has been shown to inhibit superoxide release from neutrophils stimulated by chemoattractants such as the synthetic mimic of bacterial peptides, f-met-leu-phe (fMLP), and the complement component $C_5a$ (Cronstein, B. N. et al., *J. Immunol.*, 135, 1366–1371 (1985)). Adenosine can decrease the greatly enhanced oxidative burst of PMNs (neutrophils) first primed with TNFα (an inflammatory cytokine) and then exposed to a second stimulus such as f-met-leu-phe (Sullivan, G. W. et al., *Clin. Res.* 41, 172A (1993)). There is evidence that in vivo adenosine has anti-inflammatory activity (Firestein, G. S. et al., *Clin. Res.*, 41, 170A (1993); and Cronstein, B. N. et al., *Clin. Res.*, 41, 244A (1993)). Additionally, it has been reported that adenosine can decrease the rate of HIV replication in a T-cell line (Sipka, S. et al., *Acta. Biochim. Biopys. Hung.*, 23, 75–82 (1988)).

It has been suggested that there is more than one subtype of adenosine receptor on neutrophils that have opposite effects on superoxide release (Cronstein, B. N. et al., *J. Clin. Invest.*, 85, 1150–1157 (1990)). The existence of the $A_{2A}$ receptor on neutrophils was originally demonstrated by Van Calker et al. (Van Calker, D. et al., *Eur. J. Pharmacology*, 206, 285–290 (1991)).

There has been progressive development of compounds that are more and more potent and selective as agonists of $A_{2A}$ adenosine receptors based on radioligand binding assays and physiological responses. Initially, compounds with little or no selectivity for $A_{2A}$ receptors were used, such as adenosine itself or 5'-carboxamides of adenosine, such as 5'-N-ethylcarboxamidoadenosine (NECA) (Cronstein, B. N. et al., *J. Immunol.*, 135, 1366–1371 (1985)). Later it was shown that addition of 2-alkylamino substituents increased potency and selectivity, e.g., CV1808 and CGS21680 (Jarvis, M. F. et al., *J. Pharmacol. Exp. Ther.*, 251, 888–893 (1989)). 2-Alkoxy-substituted adenosine derivatives such as WRC-0090 are even more potent and selective as agonists on the coronary artery $A_{2A}$ receptor (Ukena, M. et al., *J. Med. Chem.*, 34, 1334–1339 (1991)). The 2-alkylhydrazino adenosine derivatives, e.g., SHA 211 (also called WRC-0474) have also been evaluated as agonists at the coronary artery $A_{2A}$ receptor (Niiya, K. et al., *J. Med. Chem.*, 35, 4557–4561 (1992)).

There is one report of the combination of relatively nonspecific adenosine analogs, R-phenylisopropyladenosine (R-PIA) and 2-chloroadenosine (Cl-Ado) with a phosphodiesterase (PDE) inhibitor resulting in a lowering of neutrophil oxidative activity (Iannone, M. A. et al., in *Topics and Perspectives in Adenosine Research*, E. Gerlach et al., Eds., Springer-Verlag, Berlin, 286–298 (1987)). However, R-PIA and Cl-Ado analogs are actually more potent activators of Al adenosine receptors than of $A_{2A}$ adenosine receptors and, thus, are likely to cause side effects due to activation of $A_1$ receptors on cardiac muscle and other tissues causing effects such as "heart block".

Linden et al. (U.S. Pat. No. 5,877,180) is based on the discovery that inflammatory diseases may be effectively treated by the administration of drugs which are selective agonists of $A_{2A}$ adenosine receptors, preferably in combination with a phosphodiesterase inhibitor. An embodiment of the Linden et al. invention provides a method for treating inflammatory diseases by administering an effective amount of an $A_{2A}$ adenosine receptor of the following formula:

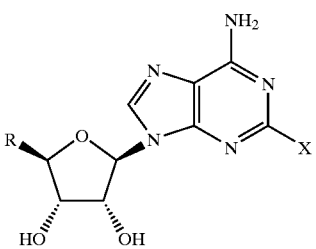

wherein X is a group selected from the group consisting of —OR$^1$, —NR$^2$R$^3$, and —NH—N=R$^4$;

wherein R$^1$ is C$_{1-4}$-alkyl; C$_{1-4}$-alkyl substituted with one or more C$_{1-4}$-alkoxy groups, halogens (fluorine, chlorine or bromine), hydroxy groups, amino groups, mono(C$_{1-4}$-alkyl) amino groups, di(C$_{1-4}$-alkyl)amino groups or C$_{6-10}$-aryl groups (wherein the aryl groups may be substituted with one or more halogens (fluorine, chlorine or bromine), C$_{1-4}$-alkyl groups, hydroxy groups, amino groups, mono(C$_{1-4}$-alkyl) amino groups or di(C$_{1-4}$ alkyl)amino groups); C$_{6-10}$-aryl; or C$_{6-10}$-aryl substituted with one or more halogens (fluorine, chlorine or bromine), hydroxy groups, amino groups, mono (C$_{1-4}$-alkyl)amino groups or di(C$_{1-4}$-alkyl)amino groups or C$_{1-4}$-alkyl groups;

one of R$^2$ and R$^3$ has the same meaning as R$^1$ and the other is hydrogen;

R$^4$ is a group having the formula:

wherein each of R$^5$ and R$^6$ independently may be hydrogen, C$_{3-7}$-cycloalkyl or any of the meanings of R$^1$, provided that R$^5$ and R$^6$ are not both hydrogen; and R is —CH$_2$OH, —CH$_2$H, —CO$_2$R$^7$ or —C(=P)NR$^8$R$^9$; wherein R$^7$ has the same meaning as R$^1$ and wherein R$^8$ and R$^9$ have the same meanings as R$^5$ and R$^6$ and R$^8$ and R$^9$ may both be hydrogen.

In a preferred embodiment, the Linden et al. invention involves the administration of a Type IV phosphodiesterase (PDE) inhibitor in combination with the A$_{2A}$ adenosine receptor agonist. The Type IV phosphodiesterase (PDE) inhibitor can be racemic and optically active 4-(polyalkoxyphenyl)-2-pyrrolidones of the following formula:

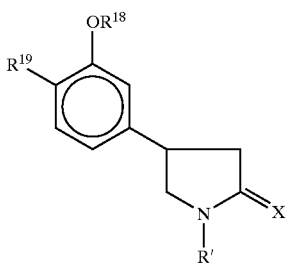

(disclosed and described in U.S. Pat. No. 4,193,926) wherein R$^{18}$ and R$^{19}$ each are alike or different and are hydrocarbon radicals having up to 18 carbon atoms with at least one being other than methyl, a heterocyclic ring or alkyl of 1–5 carbon atoms which is substituted by one or more of halogen atoms, hydroxy, carboxy, alkoxy, alkoxy- carbonyl or an amino group; amino; R' is a hydrogen atom, alkyl, aryl or acyl; and X is an oxygen atom or a sulfur atom.

Rolipram is an example of a suitable Type IV phosphodiesterase or PDE inhibitor included within the above formula. Rolipram has the following structure:

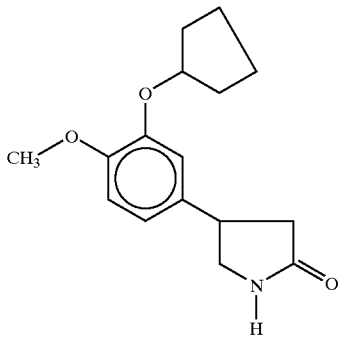

SUMMARY OF THE INVENTION

The present invention provides a method to protect mammalian tissue from the effects of the inflammatory response. This treatment is achieved by the administration of certain agonists of A$_{2A}$ adenosine receptors, preferably in combination with Rolipram or Rolipram derivatives that are Type IV phosphodiesterase or PDE inhibitors.

Accordingly, one aspect of the present invention is to provide a novel and improved method for treating the inflammatory response to pathological agents and conditions, such as trauma.

It is another aspect of the present invention to provide novel and improved compositions for the treatment of the inflammatory response and, in some cases, the underlying disease.

It is another aspect of the present invention to provide novel and improved compositions for the treatment of the inflammatory response, which are rapidly metabolized or broken down to provide less active or inactive metabolites when they come in contact with blood or other physiological fluids.

It is another aspect of the present invention to provide compounds that are short acting coronary vasodilatators for pharmacological stress imaging These and other aspects, which will become better understood during the course of the following detailed description, have been achieved by the inventors' discovery of improved compositions and methods for effectively treating inflammatory conditions by administration of an agonist of an A$_{2A}$ adenosine receptor optionally, in combination with Rolipram or a Rolipram derivative that is a Type IV phosphodiesterase (PDE) inhibitor.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
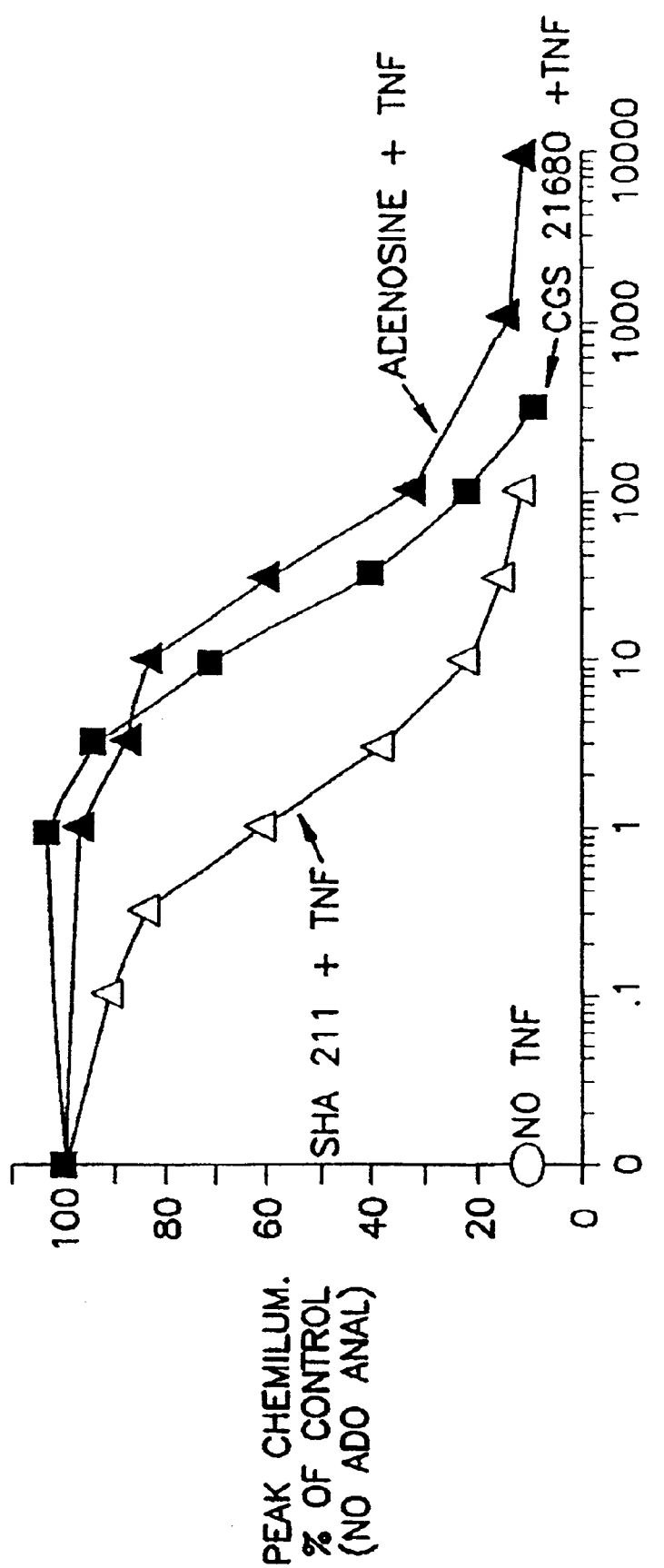
FIG. 1 illustrates the relative potencies of adenosine analogs to modulate TNF$_\alpha$-primed fMLP-stimulated polymorphonuclear cell (PMN) chemiluminescence as a measure of PMN production of oxidative products (0, no TNFα; ∆, WRC-0474 [SHA 211]+TNFα; □, GCS 21680+TNFα; and ▲, adenosine+TNFα)

Thus, in a first embodiment, the present invention provides a method comprising treating an inflammatory response in a mammal in need of such treatment by administering an effective amount of a compound formula (I):

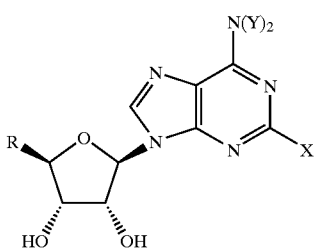

wherein X is a group selected from the group consisting of —$OR^1$, —$NR^2R^3$, —C≡C—Z and —NH—N=$R^4$;

each Y is individually H, $C_1$-$C_6$ alkyl, $C_3$-$C_7$ cycloalkyl, phenyl or phenyl $C_1$-$C_3$ alkyl;

$R^1$ is (a) $C_{1-4}$-alkyl; (b) $C_{1-4}$-alkyl substituted with one or more $C_{1-4}$-alkoxy groups, halogens (fluorine, chlorine or bromine), hydroxy groups, amino groups, mono($C_{1-4}$-alkyl) amino groups, di($C_{1-4}$-alkyl)amino groups or $C_{6-10}$-aryl groups wherein the aryl groups may be substituted with one or more halogens (fluorine, chlorine or bromine), $C_{1-4}$-alkyl groups, hydroxy groups, amino groups, mono($C_{1-4}$-alkyl) amino groups or di($C_{1-4}$-alkyl)amino groups); (c) $C_{6-10}$-aryl; or (d) $C_{6-10}$-aryl substituted with one or more halogens (fluorine, chlorine or bromine), hydroxy groups, amino groups, mono($C_{1-4}$-alkyl)amino groups, di($C_{1-4}$-alkyl)amino groups or $C_{1-4}$-alkyl groups;

one of $R^2$ and $R^3$ has the same meaning as $R^1$ and the other is hydrogen; or $R^4$ is a group having the formula (II)

wherein each of $R^5$ and $R^6$ independently may be hydrogen, $C_{3-7}$-cycloalkyl or any of the meanings of $R^1$, provided that $R^5$ and $R^6$ are not both hydrogen;

R is $CH_2OH$, $CH_3$, $CO_2R^7$ or C(=O)$NR^8R^9$ wherein $R^7$ has the same meaning as $R^2$ and wherein $R^8$ and $R^9$ have the same meanings as $R^5$ and $R^6$ or $R^8$ and $R^9$ are both H;

Z has one of the following meanings:

a) $C_6$-$C_{10}$ aryl, optionally substituted with one to three halogen atoms, $C_1$-$C_6$ alkyl, $C_1$-$C_6$ haloalkyl, $C_1$-$C_6$ alkoxy, $C_1$-$C_6$ haloalkoxy, $C_2$-$C_6$ alkoxycarbonyl, $C_2$-$C_6$ alkoxyalkyl, $C_1$-$C_6$ alkylthio, thio, CHO, cyanomethyl, nitro, cyano, hydroxy, carboxy, $C_2$-$C_6$ acyl, amino $C_1$-$C_3$ monoalkylamino, $C_2$-$C_6$ dialkylamino, methylenedioxy or aminocarbonyl;

b) a group of formula —$(CH_2)_m$-Het wherein m is 0 or an integer from 1 to 3 and Het is 5 or 6 membered heterocyclic aromatic or non-aromatic ring, optionally benzocondensed, containing 1 to 3 heteroatoms selected from nonperoxide oxygen, nitrogen or sulphur, linked through a carbon atom or through a nitrogen atom;

c) $C_3$-$C_7$ cycloalkyl optionally containing unsaturation or $C_2$-$C_4$ alkenyl;

d)

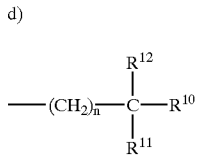

$R^{10}$ is hydrogen, methyl or phenyl;

$R^{12}$ is hydrogen, $C_1$-$C_6$ linear or branched alkyl, $C_5$-$C_6$ cycloalkyl or $C_3$-$C_7$ cycloalkenyl, phenyl-$C_1$-$C_2$-alkyl or $R^{10}$ and $R^{12}$, taken together, form a 5 or 6-membered carbocyclic ring or $R^3$ is hydrogen and $R^2$ and $R^4$, taken together, form an oxo group or a corresponding acetalic derivative;

$R^{11}$ is OH, $NH_2$ dialkylamino, halogen, cyano;

n is 0 or 1 to 4; or e) $C_1$-$C_{16}$ alkyl, optionally comprising 1–2 double bonds, O, S or NY; or a pharmaceutically acceptable salt thereof.

Examples of suitable $C_{6-10}$-aryl groups include phenyl and naphthyl.

Preferably, in the compound of formula (I), X is a group of the formula (III)

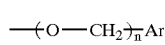 (III)

wherein n is an integer from 1–4, preferably 2, and Ar is a phenyl group, tolyl group, naphthyl group, xylyl group or mesityl group. Most preferably Ar is a para-tolyl group and n=2.

Preferably, in the compound of formula (I), X is a group of the formula (IV)

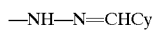 (IV)

wherein Cy is a $C_{3-7}$-cycloalkyl group, preferably cyclohexyl or a $C_{1-4}$ alkyl group, preferably isopropyl.

Preferably, in the compound of formula (I), X is a group of the formula (VII)

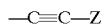 (VII)

wherein Z is $C_3$–$C_6$ alkyl, hydroxy $C_2$–$C_6$ alkyl or (phenyl)(hydroxymethyl).

Specific examples of such compounds of formula (I) include WRC-0470, WRC-0474 [SHA 211], WRC-0090 and WRC-0018, shown below:

WRC-0470
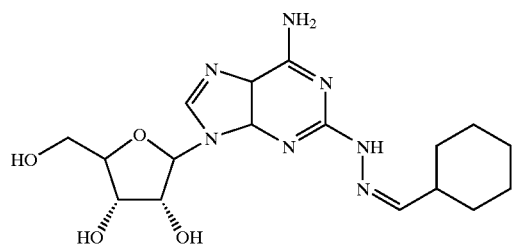

WRC-0474
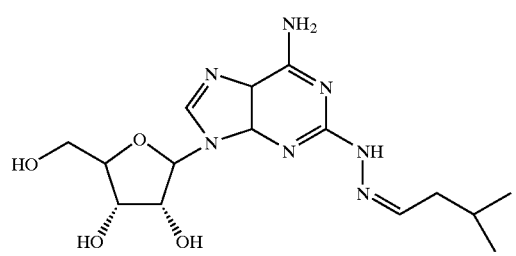

WRC-0090
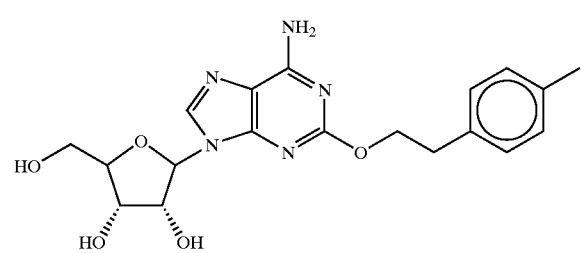

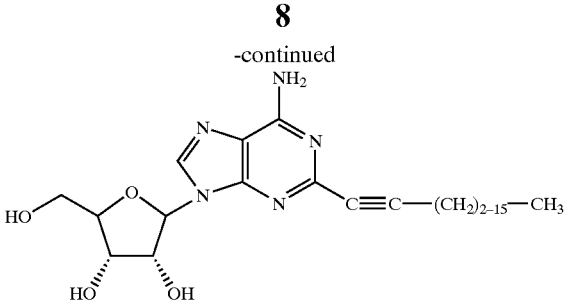
WRC-0018

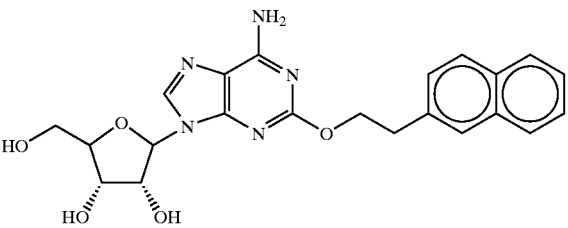

Wherein the H on CH$_2$OH can optionally be replaced by ethylaminocarbonyl. Of these specific examples, WRC-0474[SHA 211] and WRC-0470 are particularly preferred.

Such compounds may be synthesized as described in: Olsson et al. (U.S. Pat. Nos. 5,140,015 and 5,278,150); Cristalli (U.S. Pat. No. 5,593,975); Miyasaka et al. (U.S. Pat. No. 4,956,345); Hutchinson, A. J. et al., *J. Pharmacol. Exp. Ther.*, 251, 47 (1989); Olsson, R. A. et al., *J. Med. Chem.*, 29, 1683 (1986); Bridges, A. J. et al., *J. Med. Chem.*, 31, 1282 (1988); Hutchinson, A. J. et al., *J. Med. Chem.*, 33, 1919 (1990); Ukeeda, M. et al., *J. Med. Chem.*, 34, 1334 (1991); Francis, J. E. et al., *J. Med. Chem.*, 34, 2570 (1991); Yoneyama, F. et al., *Eur. J. Pharmacol.*, 213, 199–204 (1992); Peet, N. P. et al., *J. Med. Chem.*, 35, 3263 (1992); and Cristalli, G. et al., *J. Med. Chem.*, 35, 2363 (1992); all of which are incorporated herein by reference.

In another embodiment the present invention provides a method comprising treating an inflammatory response in a mammal in need of such treatment by administering an effective amount of a compound having formula (VI):

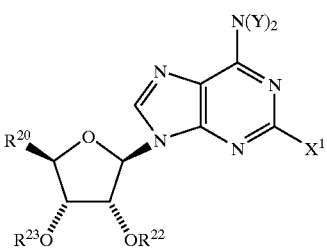 (VI)

wherein $X^1$ is —$N^{13}R^{14}$;
$R^{13}$ is hydrogen or $C_{1-4}$-alkyl; and $R^{14}$ is
(a) $C_{1-4}$-alkyl;
(b) $C_{1-4}$-alkyl substituted with one or more $C_{1-4}$-alkoxy, halogen, hydroxy, amino, mono($C_{1-4}$-alkyl)amino, di($C_{1-4}$-alkyl)amino or $C_{6-10}$-aryl wherein aryl is optionally substituted with one or more halogen, hydroxy, amino, $C_{1-4}$-alkyl, $R^{15}$OOC—($C_{1-4}$-alkyl)—, $R^{16}R^{17}$NC(=O)—($C_{1-4}$alkyl)—, mono($C_{1-4}$-alkyl) amino or di($C_{1-4}$ alkyl)amino;
(c) $C_{6-10}$-aryl; or
(d) $C_{6-10}$-aryl substituted with one or more halogen, hydroxy, amino, mono($C_{1-4}$-alkyl)amino, di($C_{1-4}$ alkyl) amino or $C_{1-4}$-alkyl;

wherein each Y is individually H, $C_1$–$C_6$ alkyl, $C_{3-7}$-cycloalkyl, phenyl or phenyl $C_{1-3}$ alkyl;

$R^{20}$ is —C(=O)$NR^{16}R^{17}$, —$COOR^{15}$, or —$CH_2OR^{15}$;

wherein each of $R^{16}$ and $R^{17}$ are independently;

(a) hydrogen;

(b) $C_{3-7}$-cycloalkyl;

(c) $C_{1-4}$-alkyl;

(d) $C_{1-4}$-alkyl substituted with one or more $C_{1-4}$-alkoxy, halogen, hydroxy, —$COOR^{21}$, amino, mono($C_{1-4}$-alkyl)amino, di($C_{1-4}$-alkyl)amino or $C_{6-10}$-aryl wherein aryl is optionally substituted with one or more halogen, $C_{1-4}$-alkyl, hydroxy, amino, mono($C_{1-4}$-alkyl)amino or di($C_{1-4}$ alkyl)amino;

(e) $C_{6-10}$-aryl; or (f) $C_{6-10}$-aryl substituted with one or more halogen, hydroxy, amino, mono($C_{1-4}$-alkyl)amino, di($C_{1-4}$ alkyl)amino or $C_{1-4}$-alkyl;

$R^{22}$ and $R^{23}$ independently represent hydrogen, lower alkanoyl, lower alkoxy-lower alkanoyl, aroyl, carbamoyl or mono- or di-lower alkylcarbamoyl; and $R^{15}$ and $R^{21}$ are independently hydrogen, $C_{1-4}$-alkyl, $C_{6-10}$-aryl or $C_{6-10}$-aryl($C_{1-4}$-alkyl); or a pharmaceutically acceptable salt thereof.

In one embodiment, at least one of $R^{13}$ and $R^{14}$ is $C_{1-4}$-alkyl substituted with one or more $C_{1-4}$-alkoxy, halogen, hydroxy, amino, mono($C_{1-4}$-alkyl)amino, di($C_{1-4}$-alkyl)amino or $C_{6-10}$-aryl wherein aryl is optionally substituted with one or more halogen, hydroxy, amino, $C_{1-4}$-alkyl, $R^{15}OOC(C_{1-4}$-alkyl), mono($C_{1-4}$-alkyl)amino or di($C_{1-4}$ alkyl)amino.

In another embodiment, at least one of $R^{16}$ and $R^{17}$ is $C_{1-4}$-alkyl substituted with one or more $C_{1-4}$-alkoxy, halogen, hydroxy, amino, mono($C_{1-4}$-alkyl)amino, di($C_{1-4}$-alkyl)amino or $C_{6-10}$-aryl wherein aryl is optionally substituted with one or more halogen, hydroxy, amino, $C_{1-4}$-alkyl, $R^{15}OOC$—($C_{1-4}$-alkyl), mono($C_{1-4}$-alkyl)amino or di($C_{1-4}$ alkyl)amino.

In another embodiment, at least one of $R^{13}$ and $R^{14}$ is $C_{6-10}$-aryl substituted with one or more halogen, hydroxy, amino, mono($C_{1-4}$-alkyl)amino, di($C_{1-4}$ alkyl)amino or $C_{1-4}$-alkyl.

In another embodiment, at least one of $R^{16}$ and $R^{17}$ is $C_{6-10}$-aryl substituted with one or more halogen, hydroxy, amino, mono($C_{1-4}$-alkyl)amino, di($C_{1-4}$ alkyl)amino or $C_{1-4}$-alkyl.

In a preferred combination, $R^{16}$ is hydrogen and $R^{17}$ is $C_{1-4}$-alkyl, cyclopropyl or hydroxy-$C_{2-4}$-alkyl. A preferred $R^{13}$ group is $C_{1-4}$-alkyl substituted with $C_{6-10}$-aryl, that is in turn substituted with $R^{15}OOC$—($C_{1-4}$-alkyl).

A preferred compound having formula (VI) is:

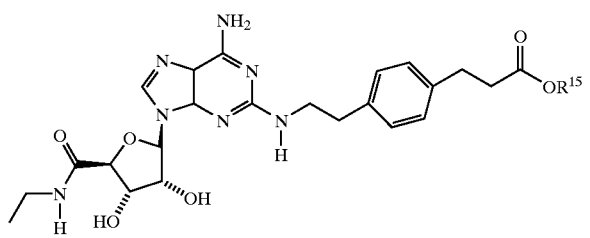

wherein $R^{15}$ is hydrogen, methyl, ethyl, n-propyl or isopropyl. More preferred is a compound wherein the $R^{15}$ group is methyl or ethyl. The most preferred $R^{15}$ group is methyl.

Two compounds that are particularly useful in practicing the present invention have the formula:

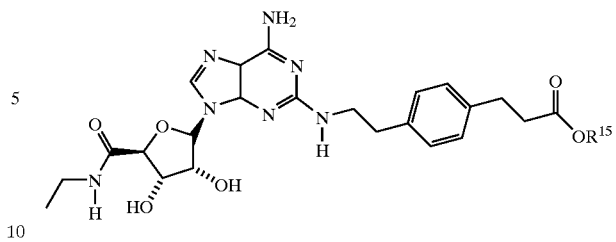

wherein $R^{15}$ is hydrogen (acid, CGS21680) and where $R^{15}$ is methyl (ester, JR2171).

The compounds of the invention having formula (VI) may be synthesized as described in: U.S. Pat. No. 4,968,697 or *J. Med. Chem.*, 33 1919–1924, (1990).

The present method also includes the administration of a Type IV phosphodiesterase (PDE) inhibitor in combination with the compound of formula (I). Examples of Type IV phosphodiesterase (PDE) inhibitors include those disclosed in U.S. Pat. No. 4,193,926, and WO 92-079778, and Molnar-Kimber, K. L. et al., *J. Immunol.*, 150, 295A (1993), all of which are incorporated herein by reference.

Specifically, the suitable Type IV phosphodiesterase (PDE) inhibitors include racemic and optically active 4-(polyalkoxyphenyl)-2-pyrrolidones of general formula (V)

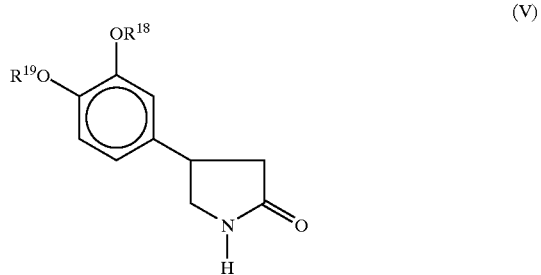

(disclosed and described in U.S. Pat. No. 4,193,926) wherein $R^{18}$ and $R^{19}$ each are alike or different and are hydrocarbon radicals having up to 18 carbon atoms with at least one being other than methyl, a heterocyclic ring or alkyl of 1–5 carbon atoms which is substituted by one or more of halogen atoms, hydroxy, carboxy, alkoxy, alkoxy-carbonyl or an amino group or amino.

Examples of hydrocarbon $R^{18}$ and $R^{19}$ groups are saturated and unsaturated, straight-chain and branched alkyl of 1–18, preferably 1–5, carbon atoms, cycloalkyl and cycloalkylalkyl, preferably 3–7 carbon atoms, and aryl and aralkyl, preferably of 6–10 carbon atoms, especially monocyclic.

Examples of alkyl are methyl, ethyl, propyl, isopropyl, butyl, isobutyl, tert-butyl, pentyl, 2-methylbutyl, 2,2-dimethylpropyl, hexyl, heptyl, octyl, nonyl, 1,2-dimethylheptyl, decyl, undecyl, dodecyl and stearyl, with the proviso that when one of $R^{18}$ and $R^{19}$ is methyl, the other is a value other than methyl. Examples of unsaturated alkyl groups are alkenyl and alkynyl, e.g., vinyl, 1-propenyl, 2-propenyl, 2-propynyl and 3-methyl-2-propenyl.

Examples of cycloalkyl and cycloalkylalkyl which preferably contain a total of 3–7 carbon atoms are cyclopropyl, cyclopropylmethyl, cyclopentyl and cyclohexyl.

Examples of aryl and aralkyl are phenyl and benzyl, which are preferred, and tolyl, xylyl, naphthyl, phenethyl and 3-phenylpropyl.

Examples of heterocyclic $R^{18}$ and $R^{19}$ groups are those wherein the heterocyclic ring is saturated with 5 or 6 ring members and has a single O, S or N atom as the hetero atom, e.g., 2- and 3-tetrahydrofuryl, 2- and 3-tetrahydropyranyl, 2- and 3-tetrahydrothiophenyl, pyrrolidino, 2- and 3-pyrrolidyl, piperidino, 2-, 3- and 4-piperidyl, and the corresponding N-alkyl-pyrrolidyl and piperidyl wherein alkyl is of 1–4 carbon atoms. Equivalents are heterocyclic rings having fewer or more, e.g., 4 and 7, ring members, and one or more additional hetero atoms as ring members, e.g., morpholino, piperazino and N-alkylpiperazino.

Examples of substituted alkyl $R^{18}$ and $R^{19}$ groups, preferably of 1–5 carbon atoms, are those mono- or polysubstituted, for example, by halogen, especially fluorine, chlorine and bromine. Specific examples of such halogen-substituted alkyl are 2-chloroethyl, 3-chloropropyl, 4-bromobutyl, difluoromethyl, trifluoromethyl, 1,1,2-trifluoro-2-chloroethyl, 3,3,3-trifluoropropyl, 2,2,3,3,3-pentafluoropropyl and 1,1,1,3,3,3-hexafluoro-2-propyl. Examples of other suitable substituents for such alkyl groups are hydroxy groups, e.g., 2-hydroxyethyl or 3-hydroxypropyl; carboxy groups, e.g., carboxymethyl or carboxyethyl; alkoxy groups, wherein each alkoxy group contains 1–5 carbon atoms, e.g., ethoxymethyl, isopropoxymethyl, 2-methoxyethyl, 2-isopropoxyethyl, 2-butyoxyethyl, 2-isobutyoxyethyl, and 3-pentoxypropyl.

Also suitable as preferably terminal-positioned substituents on alkyl groups of 1–5 carbon atoms are alkoxycarbonyl of 1–5 carbon atoms in the alkoxy group. Examples of such alkoxycarbonyl substituted alkyl-groups are ethoxycarbonylmethyl and 2-butoxycarbonylethyl.

Alkyl groups of 1–5 carbon atoms can also be substituted, e.g., in the A T and preferably terminal position with amino groups wherein the nitrogen atom optionally is mono- or disubstituted by alkyl, preferably of 1–5 carbon atoms or is part of a 4- to 7-membered ring.

Rolipram and its analogues are specific examples of preferred Type IV phosphodiesterase inhibitors.

Among the inflammatory responses that can be treated (including inhibited, blocked or treated prophylactically) with a compound of formula (I), optionally with a Type IV PDE inhibitor, are inflammation due to (a) autoimmune stimulation (autoimmune diseases), such as lupus erythematosus, multiple sclerosis, infertility from endometriosis, gout, type I diabetes mellitus including the destruction of pancreatic islets leading to diabetes and the inflammatory consequences of diabetes, including leg ulcers, Crohn's disease, ulcerative colitis, inflammatory bowel disease, osteoporosis and rheumatoid arthritis;

(b) allergic diseases such as asthma, hay fever, rhinitis, vernal conjunctivitis and other eosinophil-mediated conditions;

(c) skin diseases such as psoriasis, contact dermatitis, eczema, infectious skin ulcers, open wounds, cellulitis or burns;

(d) infectious diseases including sepsis, septic shock, encephalitis, infectious arthritis, endotoxic shock, gram negative shock, Jarisch-Herxheimer reaction, shingles, toxic shock, cerebral malaria, bacterial meningitis, acute respiratory distress syndrome (ARDS), lyme disease, HIV infection, (TNFα-enhanced HIV replication, TNFα inhibition of reverse transcriptase inhibitor activity);

(e) wasting diseases: such as, cachexia secondary to cancer and HIV;

(f) organ, tissue or cell transplantation (e.g., bone marrow, cornea, kidney, lung, liver, heart, skin, pancreatic islets) including transplant rejection, and graft versus host disease;

(g) adverse effects from drug therapy, including adverse effects from amphotericin B treatment, adverse effects from immunosuppressive therapy, e.g., interleukin-2 treatment, adverse effects from OKT3 treatment, adverse effects from GM-CSF treatment, adverse effects of cyclosporine treatment, and adverse effects of aminoglycoside treatment, stomatitis and mucositis due to immunosuppression;

(h) cardiovascular conditions including circulatory diseases induced or exacerbated by an inflammatory response, such as ischemia, atherosclerosis, peripheral vascular disease, restenosis following angioplasty, inflammatory aortic aneurysm, vasculitis, stroke, spinal cord injury, congestive heart failure, hemorrhagic shock, ischemia/reperfusion injury, vasospasm following subarachnoid hemorrhage, vasospasm following cerebrovascular accident, pleuritis, pericarditis, and the cardiovascular complications of diabetes;

(i) dialysis, including pericarditis, due to peritoneal dialysis;

(j) treatment of eye inflammation such as, inflammation resulting from irritation, trauma, infection or chemical or thermal burns to the eye;

(k) treatment of skin ischemia (for example bed sores), skin lesions or burns to promote local wound healing; and (l) application to the lung, e.g., as aerosols for the treatment of pulmonary inflammation such as acute respiratory distress syndrome (ARDS), Chronic Obstructive Pulmonary Disease (COPD), asthma and pulmonary infection.

Of particular interest and efficacy is the use of the present compounds to treat inflammatory responses due to organ, tissue or cell transplantation, i.e., the transplantation of allogeneic or xenogeneic tissue into a mammalian recipient, inflammation due to autoimmune diseases and inflammatory responses due to circulatory pathologies such as ischemia, and the treatment thereof, including angioplasty, stent placement, shunt placement or grafting.

Also of particular interest and efficacy is the use of the present compounds to treat inflammatory responses in situations where a short acting or rapidly metabolized compound is useful. Examples of such use include topical treatment of skin lesions or burns to promote local wound healing without causing systemic side effects. The compounds such as JR2171 and similar esters can be rapidly broken down in blood to less potent metabolites such as, for example, CGS21680. Such short acting compounds are less likely to produce effects that might result from longer acting compounds, such as bleeding. It is believed that the ester compounds produce lower systemic side effects because they are rapidly metabolized in blood by plasma esterases.

Therefore, the esters could be useful for the topical treatment of skin lesions or burns to promote local wound healing without causing systemic side effects, such as, for example, hypotension or cardiac acceleration, secondary to systemic uptake of the compound. The rapid metabolism of the esters in blood could minimize such side effects when the compounds are administered to the eye, lung or skin to produce a local anti-inflammatory pulmonary effects with minimal systemic side effects.

While many of the compounds of formula (I) are vasodilators, and thus have been reported as useful to treat ischemia, atherosclerosis, hypertension, thrombus and the like, the anti-inflammatory activity of these compounds has not heretofore been suggested.

The invention also includes a method for binding a compound of formula (I or VI) to designated $A_{2A}$ adenosine receptor sites comprising said receptors, in vivo or in vitro, with an amount of a compound of formula (I or VI) effective to bind to said receptors. Tissue or cells comprising ligand bound receptor sites can be used to measure the selectivity of test compounds for specific receptor subtypes or can be used as a tool to identify potential therapeutic agents for the treatment of diseases or conditions associated with receptor site activation, by contacting said agents with said ligand-receptor complexes, and measuring the extent of displacement of the ligand and/or binding of the agent.

The exact dosage of the compound of formula (I or VI) to be administered will, of course, depend on the size and condition of the patient being treated, the exact condition being treated, and the identity of the particular compound of formula (I or VI) being administered. However, a suitable dosage of the compound of formula (I or VI) is 0.5 to 100 µg/kg of body weight, preferably 1 to 10 µg/kg of body weight. Typically, the compound of formula (I or VI) will be administered from 1 to 8, preferably 1 to 4, times per day.

The preferred mode of administration of the compound of formula (I or VI) may also depend on the exact condition being treated. However, most typically, the mode of administration will be oral, topical, intravenous, parenteral, subcutaneous, as an aerosol or intramuscular injection.

Of course, it is to be understood that the compound of formula (I or VI) may be administered in the form of a pharmaceutically acceptable salt. Examples of such salts include acid addition salts. Preferred pharmaceutically acceptable addition salts include salts of mineral acids, for example, hydrochloric acid, sulfuric acid, nitric acid, and the like; salts of monobasic carboxylic acids, such as, for example, acetic acid, propionic acid, and the like; salts of dibasic carboxylic acids, such as maleic acid, famaric acid, oxalic acid, and the like; and the salts of tribasic carboxylic acids, such as, carboxysuccinic acid, citric acid, and the like. In the compounds of formula (I or VI) in which R is —$CO_2H$, the salt may be derived by replacing the acidic proton of the —$CO_2H$ group with a cation such as $Na^+$, $K^+$, $NH^+_4$ mono-, di-, tri- or tetra($C_{1-4}$-alkyl)ammonium or mono-, di-, tri- or tetra($C_{2-4}$ alkanol) ammonium.

Preferred pharmaceutically acceptable addition salts include salts of mineral acids, for example, hydrochloric acid, sulfuric acid, nitric acid, and the like; salts of monobasic carboxylic acids, such as, for example, acetic acid, propionic acid, and the like; salts of dibasic carboxylic acids, such as maleic acid, fumaric acid, oxalic acid, and the like; and salts of tribasic carboxylic acids, such as, carboxysuccinic acid, citric acid, and the like.

It is also to be understood that many of the compounds of formula (I or VI) may exist as various isomers, enantiomers, and diastereomers and that the present invention encompasses the administration of a single isomer, enantiomer or diastereomer in addition to the administration of mixtures of isomers, enantiomers or diastereomers.

The compounds of formula (I or VI) can be administered orally, for example, with an inert diluent with an edible carrier. They can be enclosed in gelatin capsules or compressed into tablets. For the purposes of oral therapeutic administration, the compounds can be incorporated with excipients and used in the form of tablets, troches, capsules, elixers, suspensions, syrups, waters, chewing gums, and the like. These preparations should contain at least 0.5% by weight of the compound of formula (I or VI), but the amount can be varied depending upon the particular form and can conveniently be between 4.0% to about 70% by weight of the unit dosage. The amount of the compound of formula (I or VI) in such compositions is such that a suitable dosage will be obtained. Preferred compositions and preparations according to the present invention are prepared so that an oral dosage unit form contains between about 30 µg and about 5 mg, preferably between 50 to 500 µg, of active compound.

Tablets, pills, capsules, troches, and the like can contain the following ingredients: a binder, such as microcrystalline cellulose, gum tragacanth or gelatin; an excipient, such as starch or lactose; a disintegrating agent, such as alginic acid, Primogel, corn starch, and the like; a lubricant, such as magnesium stearate or Sterotes; a glidant, such as colloidal silicon dioxide; a sweetening agent, such as sucrose, saccharin or aspartame; or flavoring agent, such as peppermint, methyl salicylate or orange flavoring. When the dosage unit form is a capsule it can contain, in addition to the compound of formula (I or VI), a liquid carrier, such as a fatty oil.

Other dosage unit forms can contain other materials that modify the physical form of the dosage unit, for example, as coatings. Thus, tablets or pills can be coated with sugar, shellac or other enteric coating agents. A syrup may contain, in addition to the active compounds, sucrose as a sweetening agent and preservatives, dyes, colorings, and flavors. Materials used in preparing these compositions should be pharmaceutically pure and non-toxic in the amounts used.

For purposes of parenteral therapeutic administration, the compounds of formula (I or VI) can be incorporated into a solution or suspension. These preparations should contain at least 0.1% of the aforesaid compound, but may be varied between 0.5% and about 50% of the weight thereof. The amount of active compound in such compositions is such that a suitable dosage will be obtained. Preferred compositions and preparations according to the present invention are prepared so that a parenteral dosage unit contains between 30 µg to 5 mg, preferably between 50 to 500 µg, of the compound of formula (I or VI).

Solutions or suspensions of the compounds of formula (I or VI) can also include the following components: a sterile diluent, such as water for injection, saline solution, fixed oils, polyethylene glycols, glycerine, propylene glycol or other synthetic solvents: antibacterial agents, such as benzyl alcohol or methyl parabens; antioxidants, such as ascorbic acid or sodium bisulfite; chelating agents, such as ethylenediaminetetraacetic acid; buffers, such as acetates, citrates or phosphates; and agents for the adjustment of tonicity, such as sodium chloride or dextrose. The parenteral preparation can be enclosed in ampoules, disposable syringes or multiple dose vials made of glass or plastic.

Effective amounts of the Type IV phosphodiesterase inhibitor can be administered to a subject by any one of various methods, for example, orally as in a capsule or tablets, topically or parenterally in the form of sterile solutions. The Type IV phosphodiesterase inhibitors, while effective themselves, can be formulated and administered in the form of their pharmaceutically acceptable addition salts for purposes of stability, convenience of crystallization, increased solubility, and the like.

The Type IV phosphodiesterase may be administered in the form of a pharmaceutical composition similar to those described above in the context of the compound of formula (I or VI).

While dosage values will vary with the specific disease condition to be alleviated, good results are achieved when the Type IV phosphodiesterase inhibitor is administered to a subject requiring such treatment as an effective oral, parenteral or intravenous dose as described below.

For oral administration, the amount of active agent per oral dosage unit usually is 0.1–20 mg, preferably 0.5–10 mg. The daily dosage is usually 0.1–50 mg, preferably 1–30 mg p.o. For parenteral application, the amount of active agent per dosage unit is usually 0.005–10 mg, preferably 0.01–5 mg. The daily dosage is usually 0.01–20 mg, preferably 0.02–5 mg i.v. or i.m.

With topical administration, dosage levels and their related procedures would be consistent with those known in the art, such as those dosage levels and procedures described in U.S. Pat. No. 5,565,462 to Eitan et al., which is incorporated herein by reference.

It is to be understood, however, that for any particular subject, specific dosage regimens should be adjusted to the individual need and the professional judgment of the person administering or supervising the administration of the Type IV phosphodiesterase inhibitor. In some cases, the compound of formula (I or VI) will be administered for an extended period of time following the inflammatory insult, even chronically. It is to be further understood that the dosages set forth herein are exemplary only and that they do not, to any extent, limit the scope or practice of the present invention.

In a particularly preferred embodiment, the compound of formula (I or VI) and the Type IV phosphodiesterase inhibitor are coadministered together in a single dosage unit. The compound of formula (I or VI) and the Type IV phosphodiesterase inhibitor may be administered in the same type of pharmaceutical composition as those described above in the context of the compound of formula (I or VI).

By coadministering a Type IV phosphodiesterase inhibitor with the agonist of the $A_{2A}$ adenosine receptor, it is possible to dramatically lower the dosage of the $A_{2A}$ adenosine receptor agonist and the Type IV phosphodiesterase inhibitor due to a synergistic effect of the two agents. Thus, in the embodiment involving coadministration of the $A_{2A}$ adenosine receptor agonist with the Type IV phosphodiesterase inhibitor, the dosage of the $A_{2A}$ adenosine receptor agonist may be reduced by a factor of 5 to 10 from the dosage used when no Type IV phosphodiesterase inhibitor is administered. This reduces the possibility of side effects.

The compounds of the invention can be administered by inhalation from an inhaler, insufflator, atomizer or pressurized pack or other means of delivering an aerosol spray. Pressurized packs may comprise a suitable propellant such as carbon dioxide or other suitable gas. In case of a pressurized aerosol, the dosage unit may be determined by providing a value to deliver a metered amount. The inhalers, insufflators, atomizers are fully described in pharmaceutical reference books such as Remington's Pharmaceutical Sciences $16^{th}$ ed. (1980) or 18th ed. (1990) Mack Publishing Co.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The present invention will now be described in more detail in the context of the coadministration of WRC-0470, WRC-0474[SHA 211], WRC-0090 or WRC-0018 and rolipram. However, it is to be understood that the present invention may be practiced with other compounds of formula (I or VI) and other Type IV phosphodiesterase inhibitors of formula (V).

The present studies establish that anti-inflammatory doses have no toxic effects in animals; the effect of WRC-0470 to inhibit neutrophil activation is synergistic with rolipram; and intravenous infusion of WRC-0470 profoundly inhibits extravasation of neutrophils in an animal model of inflammation, an action also synergistic with rolipram. Further, the present studies establish that activation of $A_{2A}$ receptors on human monocytes strongly inhibits TNFα (an inflammatory cytokine) release. This mechanism further contributes to the anti-inflammatory action of the $A_{2A}$ adenosine receptor agonists of the present invention.

Other features of the invention will become apparent in the course of the following descriptions of exemplary embodiments which are given for illustration of the invention and are not intended to be limiting thereof.

EXAMPLES

Materials and Methods

Materials. f-Met-Leu-Phe(fMLP), luminol, and trypan blue were from Sigma Chemical. Ficoll-Hypaque was purchased from Flow Laboratories (McLean, A) and Los Alamos Diagnostics (Los Alamos, N.M.). Hanks balanced salt solution (HBSS), and limulus amebocyte lysate assay kit were from Whittaker Bioproducts (Walkersville, Md.). Human serum albumin (HSA) was from Cutter Biological (Elkhart, Ind.). Recombinant human tumor necrosis factor-alpha was supplied by Dianippon Pharmaceutical Co. Ltd. (Osaka, Japan). ZM241385 was a gift of Dr. Simon Poucher, Zeneca Pharmaceuticals (Chesire, England).

Leukocyte Preparation: Purified PMN (~98% PMN and >95% viable by trypan blue exclusion) containing <1 platelet per 5 PMN and <50 pg/ml endotoxin (limulus amebocyte lysate assay) were obtained from normal heparinized (10 Units/ml) venous blood by a one-step Ficoll-Hypaque separation procedure (Ferrante, A. et al., *J. Immunol. Meth.*, 36, 109 (1980)). Residual RBC were lysed by hypotonic lysis with iced 3 ml 0.22% sodium chloride solution for 45 seconds followed by 0.88 ml of 3% sodium chloride solution.

Chemiluminescence. Luminol-enhanced chemiluminescence, a measure of neutrophil oxidative activity, is dependent upon both superoxide production and mobilization of the granule enzyme myeloperoxidase. The light is emitted from unstable high-energy oxygen species generated by activated neutrophils. Purified PMN ($5 \times 10^5$/ml) were incubated in HBSS containing 0.1% human serum albumin (1 ml) with or without adenosine, adenosine analogs, and TNFα (1 U/mL) for 30 minutes at 37° C. in a shaking water bath. Then luminol ($1 \times 10^{-4}$ M) enhanced f-met-leu-phe (1 μM) stimulated chemiluminescence was read with a Chronolog Photometer (Chrono-log Corp., Havertown, Pa.) at 37° C. for 8 min. Chemiluminescence is reported as relative peak light emitted (=height of the curve) compared to samples with TNF and without adenosine or adenosine analogs. WRC-0474[SHA 211] was 10 times more potent than either adenosine (ADO) or CGS21680 in decreased TNFα-primed f-met-leu-phe-stimulated PMN chemiluminescence (see FIG. 1).

Synthesis of 3-(4-{2-[6-Amino-9-(5-ethylcarbamoyl-3,4-dihydroxy-tetrahydro-furan-2-yl)9H-purin-2-ylamino]-ethyl}-phenyl)-propionic acid methyl ester (JR2171). The methyl ester, JR2171, was synthesized by dissolving approximately 10.0 mg of 3-(4-{2-[6-amino-9-(5-ethylcarbamoyl-3,4-dihydroxy-tetrahydro-furan-2-yl)-9H-purin-2-ylamino]-ethyl}-phenyl)-propionic acid (CGS21680) in 5 mL 10% MeOH/$CH_2Cl_2$ and adding TMS Diazomethane (2.0 M solution in hexanes) dropwise until a yellow color persisted. After stirring for 30 minutes the solvent was removed under reduced pressure. The crude compound was then purified by HPLC using a $C_{18}$ column and a MeOH/$H_2O$ gradient, yielding 6.7 mg of compound (66% yield). Characterization by HRMS, APCI MS, $^1H$ NMR, and $^{13}C$ NMR were consistent with the putative structure.

Characterization Data:

High Resolution MS (HRMS) analysis performed by the University of Nebraska Center for Mass Spectrometry: actual=514.2408: calculated=514.2414

APCI MS data: Molecular ion=514.3

$^1$H NMR (CD$_3$OD) d 7.93 (s, 1H), 7.09 (m, 4 H), 5.88 (d, 1 H), 4.95 (m, 1 H), 4.42 (m, 1 H), 4.33 (d, 1 H), 3.58 (s, 3 H), 3.43 (m, 2 H), 3.07 (m, 2 H), 2.80 (m, 4H),2.54(t,2H), 0.96(t,3 H).

$^{13}$C NMR (CD$_3$OD) d 173.2, 170.2, 159.3, 155.6, 155.5, 137.9, 137.3, 137.1, 128.2, 127.6, 112.8, 88.2, 83.7, 72.8, 71.3, 50.2, 42.4, 34.8, 34.7, 33.3, 29.7, 12.8.

Synergy of A$_{2A}$ Adenosine Receptor Agonist and Phosphodiesterase Inhibitors. The synergy between WRC-0474 [SHA 211] and 4-(3-cyclopentyloxy-4-methoxyphenyl)-2-pyrrolidone (rolipram) was examined by measuring the effect of combined WRC-0474[SHA 211] and rolipram on TNF-primed f-met-leu-phe-stimulated suspended neutrophil superoxide release and on the oxidative burst of neutrophils adhering to matrix proteins (in this model, the PMN oxidative burst is enhanced by small concentrations of TNFα [e.g., 1 U/ml] when added prior to the addition of a second stimulus such as the peptide f-met-leu-phe).

Suspended PMN Superoxide Release. Human PMN ($1\times10^6$/ml) from Ficoll-Hypaque separation were primed for 30 minutes (37° C.) with or without rhTNF (10 U/ml), with adenosine deaminase (1 U/ml), and with or without 4-(3-cyclopentyloxy-4-methoxyphenyl)-2-pyrrolidone and SHA 211. Cytochrome c (120 $\mu$M), catalase (0.062 mg/ml) and fMLP (100 nM) were added and the samples incubated for 10 minutes more at 37° C. SOD (200 U/ml) was added to matched samples. The samples were iced and centrifuged (2000 g×10 minutes). The optical density of the supernatants was read at 550 nm against the matched SOD samples, and the nmoles of SOD-inhibitable superoxide released in 10 minutes were calculated.

Figure 2:
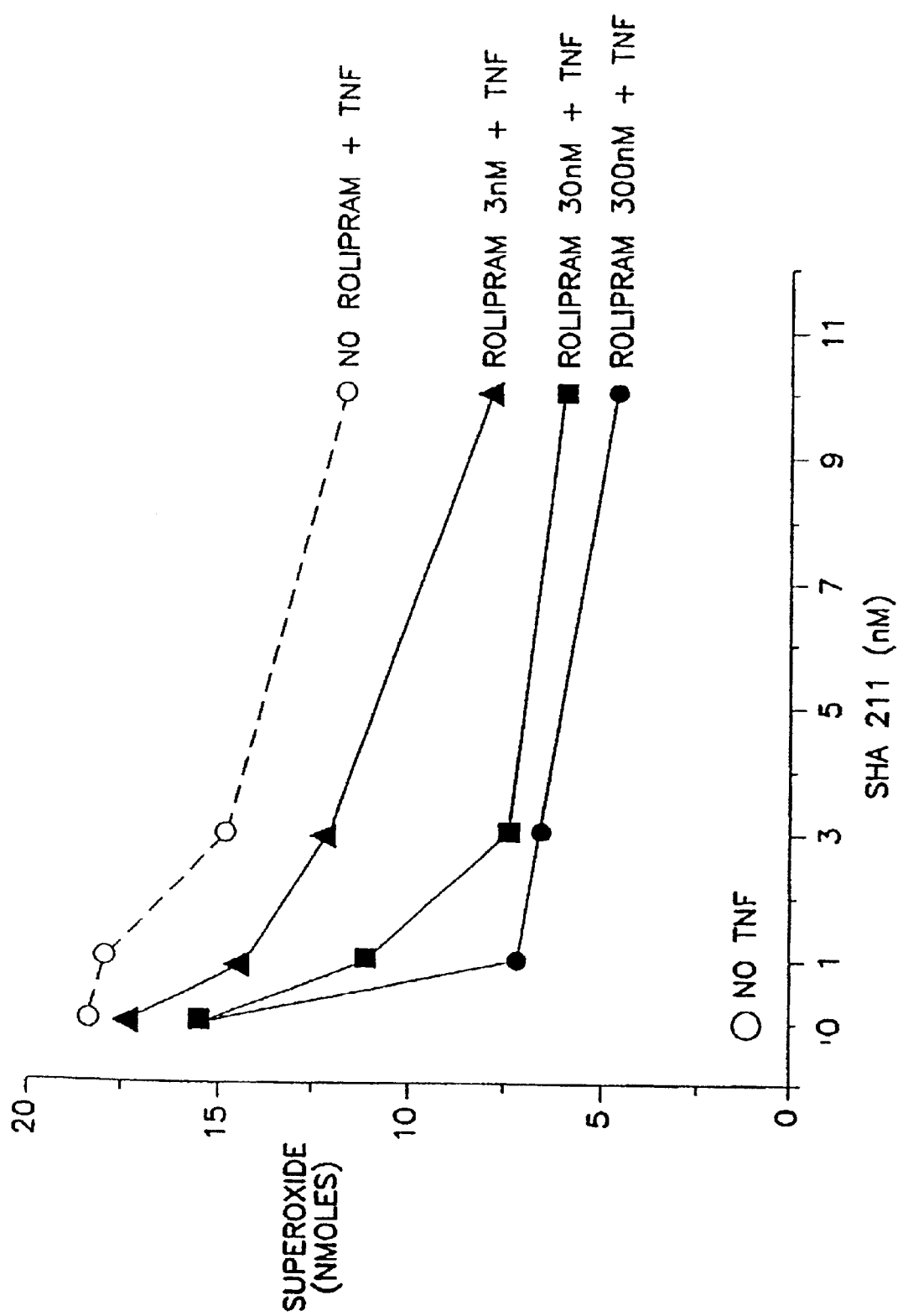
FIG. 2 illustrates the synergistic effect of WRC-0474 [SHA 211] and 4-(3-cyclopentyloxy-4-methoxyphenyl)-2-pyrrolidone (Rolipram) in inhibiting TNFα-primed (10 U/ml), fMLP-stimulated (100 nM) PMN superoxide production: 0, no 4-(3-cyclopentyloxy-4-methoxyphenyl)-2-pyrrolidone; ▲, 3 nM 4-(3-cyclopentyloxy-4-methoxyphenyl)-2-pyrrolidone; □, 30 nM 4-(3-cyclopentyloxy-4-methoxyphenyl)-2-pyrrolidone; and, 300 nM 4-(3-cyclopentyloxy-4-methoxyphenyl)-2-pyrrolidone.

A synergistic effect of WRC-0474[SHA 211] and rolipram in decreasing the TNFα-primed fMLP-stimulated PMN oxidative burst was observed (see FIG. 2).

TNFα-stimulated superoxide release of PMN adherent to a matrix protein (fibrinogen) coated surface. Human PMN ($1\times10^6$/ml) from Ficoll-Hypaque separation were incubated for 90 minutes in 1 ml of Hanks balanced salt solution containing 0.1% human serum albumin, cytochrome c (120 $\mu$M), and catalase (0.062 mg/ml) in the presence and absence of rhTNF (1 U/ml), WRC-0474[SHA 211] (10 nM) and rolipram (100 nM) in a tissue culture well which had been coated overnight with human fibrinogen. SOD (200 U/ml) was added to matched samples. The supernatants were iced and centrifuged (2000 g×10 minutes) to remove any remaining suspended cells, and the optical density of the supernatants were read at 550 nM against the matched SOD samples, and the nmoles of SOD-inhibitable superoxide released in 90 minutes were calculated.

Figure 3:
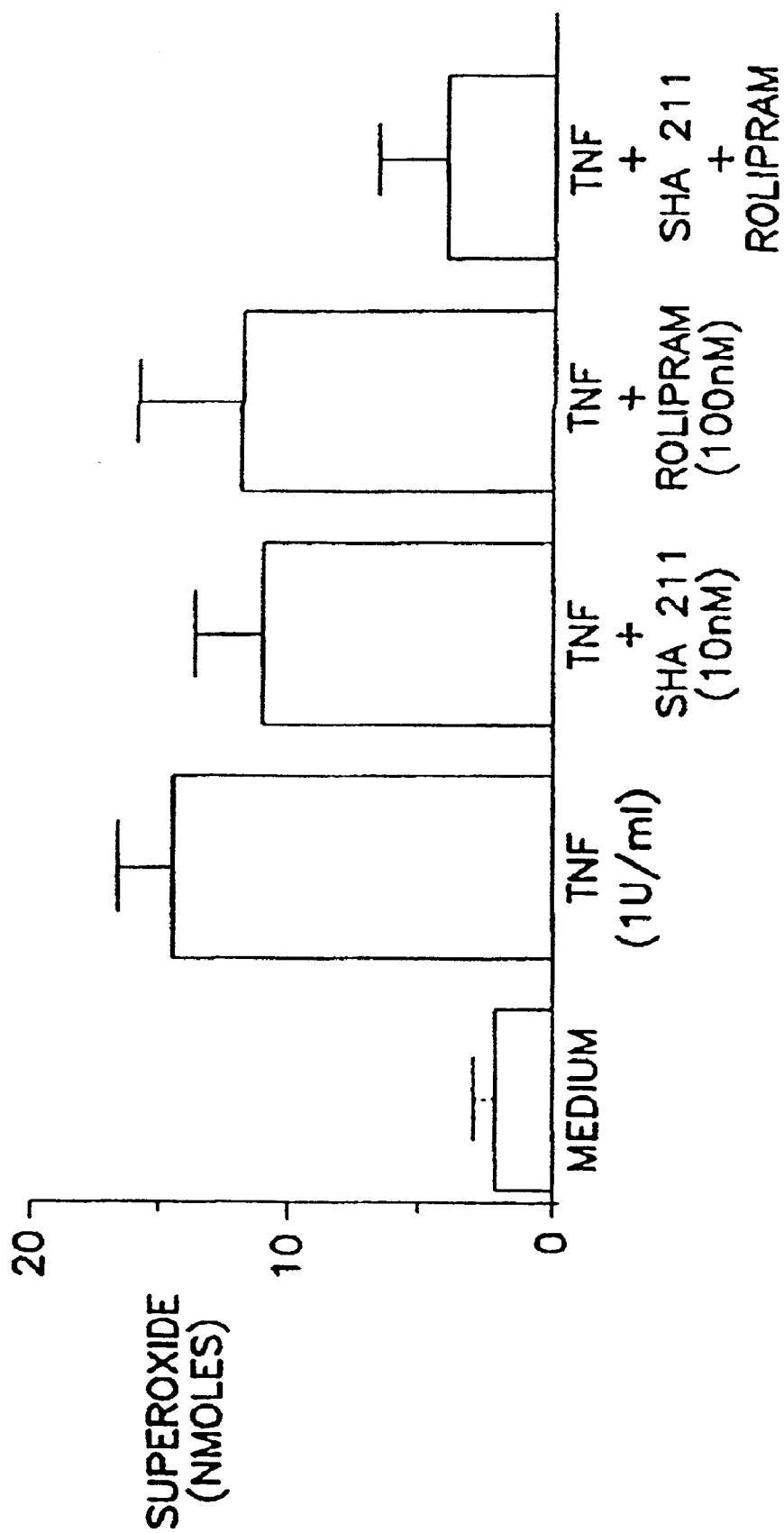
FIG. 3 illustrates the synergistic effect of WRC-0474 [SHA 211] and Rolipram in inhibiting TNFα-stimulated adherent PMN superoxide release.

A synergistic effect of WRC-0474[SHA 211] and rolipram in decreasing the TNFα-stimulated release of superoxide from PMN adherent to fibrinogen was observed (see FIG. 3).

Effect of WRC-0474[SHA 211] with and without rolipram on TNF-Stimulated PMN Adherence to a Fibrinogen-Coated Surface. Cronstein et al., *J. Immunol.* 148, 2201 (1992) reported that adenosine binding to A$_1$ receptors increases PMN adherence to endothelium and matrix proteins and binding to A$_2$ receptors decreases adherence to these surfaces when the PMN are stimulated with fMLP. Despite this, others have failed to see much of an effect of adenosine (10 $\mu$M) on TNFα-stimulated PMN adherence to matrix proteins. In contrast, adenosine dramatically decreases the oxidative burst of TNFα-stimulated PMN adhering to matrix proteins (DeLa Harpe, J., *J. Immunol.*, 143 596 (1989)). The experiments described above establish that WRC-0474[SHA 211] decreases TNF-stimulated oxidative activity of PMN adhering to fibrinogen, especially when combined with rolipram.

Figure 4:
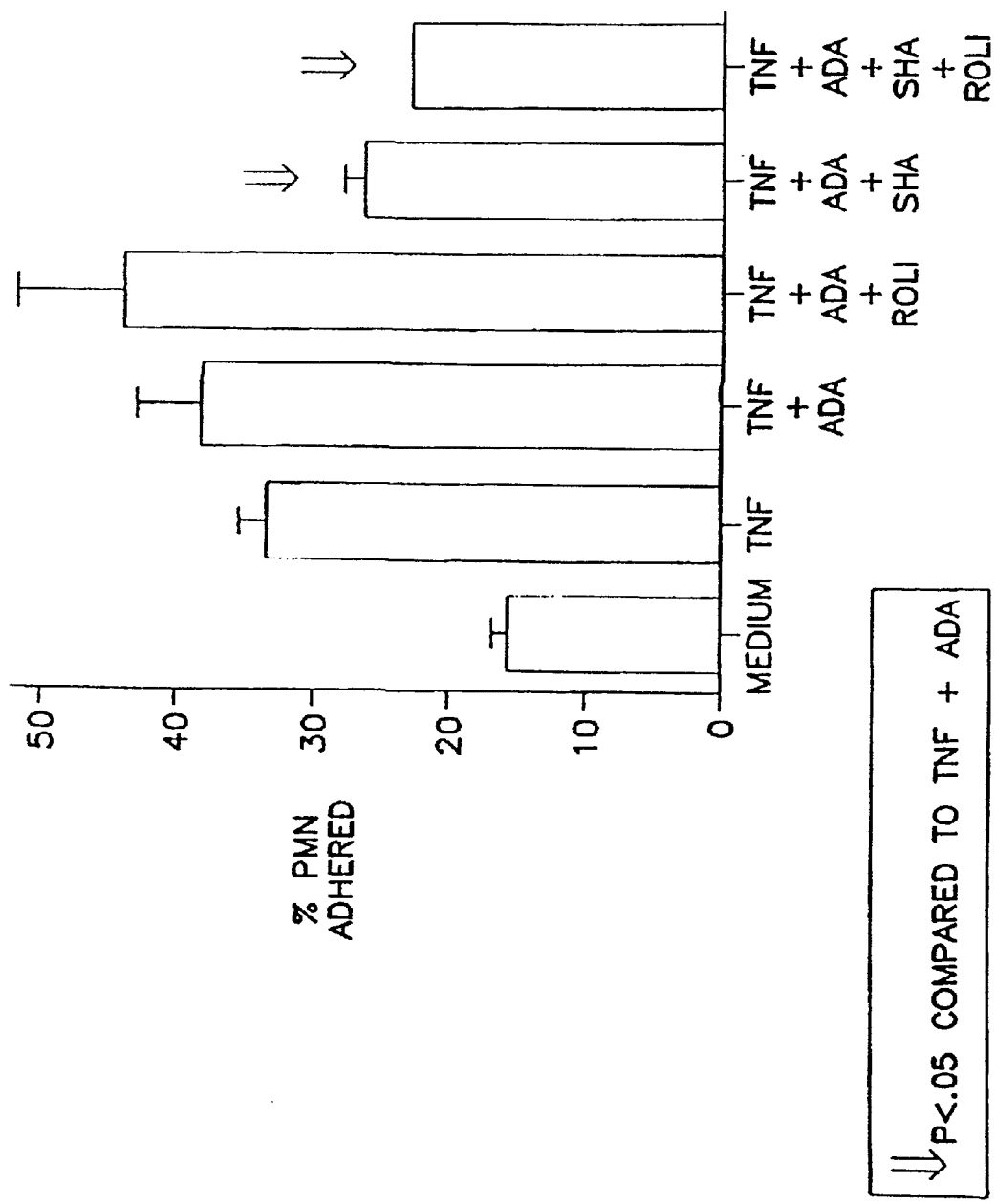
FIG. 4 illustrates the effect of WRC-0474[SHA 211] and Rolipram on TNFα-stimulated PMN adherence to a fibrinogen coated surface.

PMN adherence to fibrinogen was measured as follows as adapted from Hanlon, *J. Leukocyte Biol.*, 50, 43 (1991). Twenty-four well flat-bottomed tissue culture plates were incubated (37° C.) overnight with 0.5 ml of fibrinogen (5 mg/ml) dissolved in 1.5% NaHCO$_3$. The plates were emptied and each well washed 2× with 1 ml of normal saline. The wells were then filled with 1 ml of HBSS-0.1% human serum albumin containing PMN ($1\times10^6$/ml) with and without rhTNFα (1 U/ml), adenosine deaminase (ADA) (1 U/ML), WRC-0474[SHA 211] (10 nM), CGS21680 (30 nM), adenosine (100 nM) and rolipram (100 nM). The plates were incubated for 90 minutes at 37° C. in 5% CO$_2$. Following incubation the tissue culture wells were washed free of non-adherent cells with normal saline. The adherent monolayer of PMN was lysed with 0.1% triton-X, the amount of lactic dehydrogenase (LDH) released from the monolayer assayed (LDH kit, Sigma Co., St. Louis, Mo.), and compared to a standard curve relating the LDH content to PMN numbers. The results are shown in FIG. 4.

As a comparison to WRC-0474[SHA 211] (at only 10 nM), CGS21680 (30 nM) decreased TNF-stimulated adherence in the presence of ADA from 38% to 30% adhered (p=0.004) (see FIG. 4), and ten times as much adenosine (100 nM) decreased adherence to 28% adhered (p=0.009 compared to TNF in the presence of ADA).

Additional effects of adenosine A$_{2A}$ agonists on adherent human neutrophil oxidative activity. The bioactivity of test compounds WRC-0474[SHA 211], WRC-0470, WRC-0090 and WRC-0018 were evaluated according to the following method modified from Sullivan, G. W. et al., *Int. J. Immunopharmacol*, 17, 793–803 (1995). Neutrophils ($1\times10^6$/ml) from Ficoll-Hypaque separation were incubated for 90 minutes in 1 ml of Hanks balanced salt solution containing 0.1% human serum albumin, cytochrome c (120 $\mu$M) and catalase (0.062 mg/ml) in the presence and absence of rhTNFα (1 U/ml), WRC-0474[SHA 211], WRC-0470, WRC-0090 and WRC-0018 (3–300 nM), and rolipram (100 nM) in a tissue culture well which had been coated overnight with human fibrinogen. The supernatants were iced and centrifuged (200 g×10 min) to remove any remaining suspended cells, and the optical densities of the supernatants were read at 550 nM against matched superoxide dismutase (SOD) (200 U/ml) samples. The nmoles of SOD= inhabitable superoxide released in 90 min were calculated.

Figure 5A:
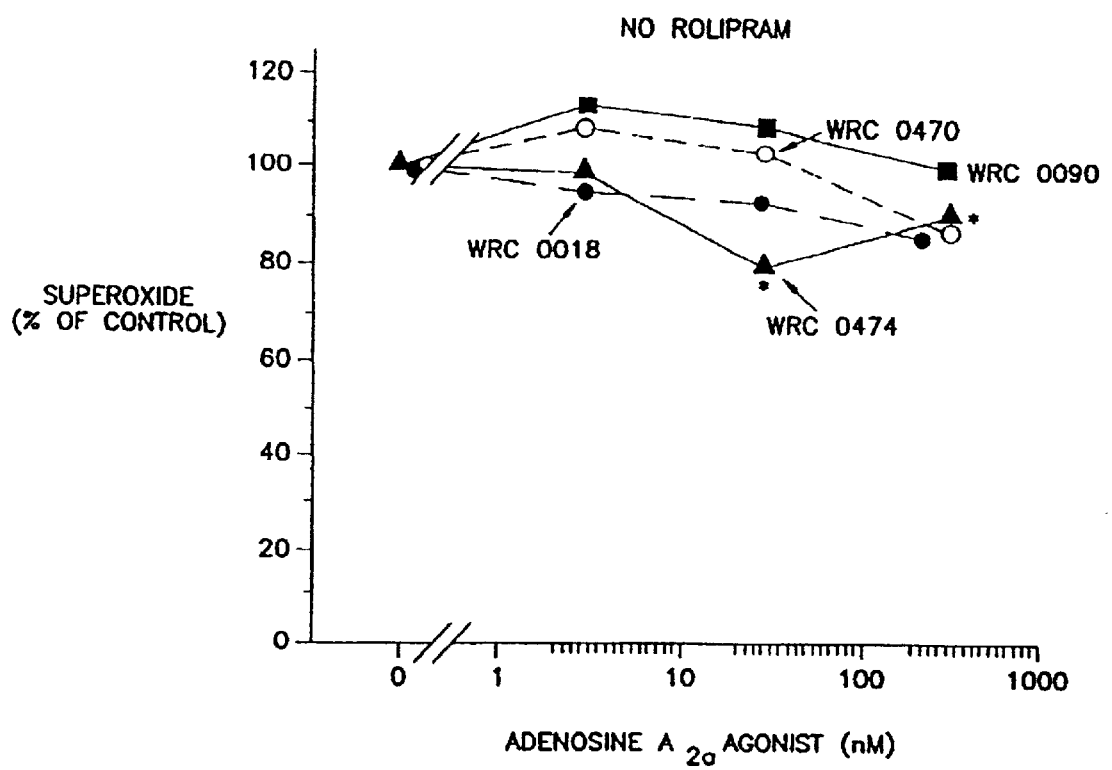
FIG. 5 illustrates synergy between $A_{2A}$ adenosine receptor agonists and Rolipram in inhibition superoxide release from TNFα-stimulated adherent human neutrophils.
Figure 5B:
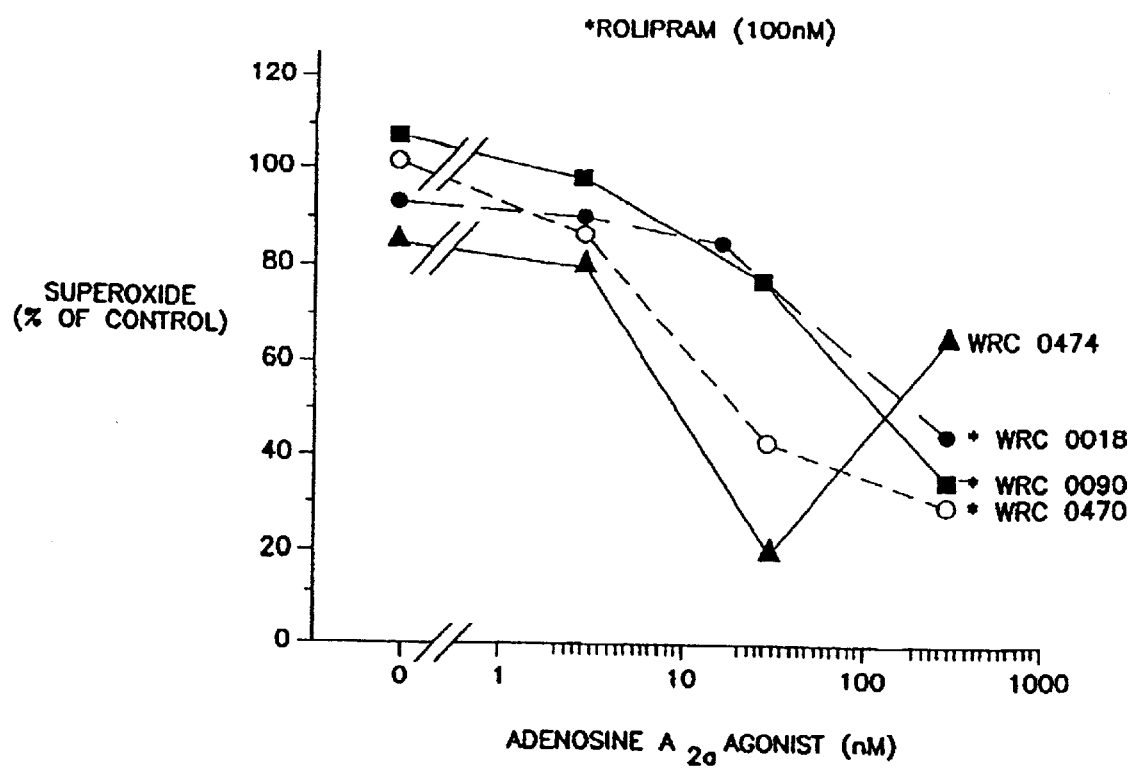

FIG. 5 shows synergy between A2A adenosine agonists and rolipram in inhibiting TNFα-stimulated adherent PMN oxidative activity (p<0.05). WRC-0474[SHA 211] (30–300 nM), WRC-0470 (300 nM), WRC-0090 (300 nM) and WRC-0018 (300 nM) combined with rolipram synergistically decreased superoxide release (p<0.05). All four compounds had some activity in the presence of rolipram. WRC-0474[SHA 211] and WRC-0470 were the most active. Nanomolar concentrations of WRC-0474[SHA 211] resulted in biphasic activity. All compounds were synergistic with rolipram to decrease TNFα-stimulated adherent PMN oxidative activity.

PMN degranulation (adherent cells). The following methods were adapted from Sullivan, G. W. and G. L. Mandell, Infect. Immun., 30, 272–280 (1980). Neutrophils ($3.1 \times 10^6$/ml) from Ficoll-Hypaque separation were incubate for 120 minutes in 1 ml of Hanks balanced salt solution containing 0.1% human serum albumin, ±rh TNFα (10 U/ml), ±WRC-0470 (3–300 nM), and ±rolipram (30 nM) in a tissue culture well which had been coated overnight with human fibrinogen. The supernatant fluids with any suspended neutrophils were harvested following incubation, centrifuged (2000×g for 10 min) to remove any suspended cells and the cell-free supernatants frozen. Release of lysozyme, a component of neutrophil primary and secondary granules was assayed. Lysis of a suspension of *Micrococcus lysodeikticus* by the "cell-free supernatant" was measured by spectrophotometric analysis (540 mm) to determine the amount of release of granule contents to the surrounding medium.

Results showed that WRC-0470 (300 nM) with rolipram (300 nM) significantly decreased TNFα-stimulated adherent neutrophil degranulation 67%; P=0.027. The data indicate that in addition to decreasing TNFα-stimulated PMN adherent and the oxidative burst of these adherent neutrophils, WRC-0470 also decreases degranulation activated PMN adhering to a biological surface.

PMN oxidative activity in whole blood. The following methods were adapted from Rothe, G. A. et al., *J. Immunol. Meth.*, 138, 133–135 (1991). Heparinized whole blood (0.8 ml) was incubated (37°; 30 min) with adenosine deaminase (ADA, 1 U/ml), catalase (14,000 U/ml), ±dihydrorhodamine 123, ±WRC-0470 (3–300 nM), ±rolipram (300 nM) and ±TNFα (10 U/ml). The primed blood samples were stimulated with fMLP (15 min), then iced, the red blood cells lysed with FACS lysing solution (Becton-Dickinson, San Jose, Calif.), washed and the leukocytes resuspended in phosphate-buffered saline (PBS). These samples containing mixed leukocytes were gated for neutrophils by forward and side scatter and the fluorescence of 10,000 neutrophils measured in the FL1 channel of a FACScan (Beckton-Dickinson) fluorescence-activated cell sorter.

Figure 6:
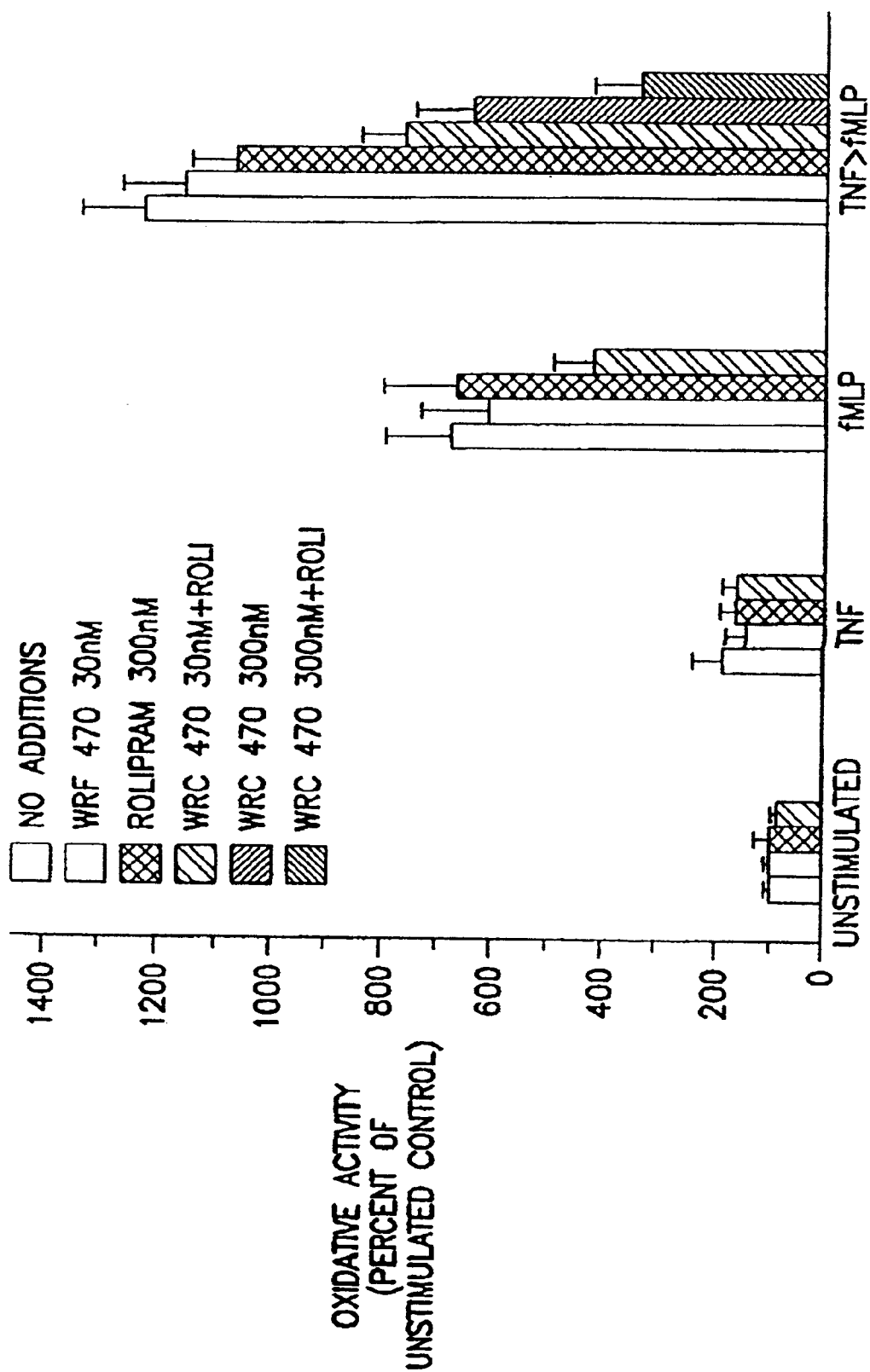
FIG. 6 illustrates the effects of WRC-0470 and Rolipram on the oxidative activity of neutrophils in whole blood.

The results are reported as relative mean fluorescence intensity in FIG. 6 of the drawings. WRC-0470 decreased oxidative activity of TNFα-primed FMLP-stimulated neutrophils in whole blood and acted synergistically with rolipram. WRC-0470 (30–300 nM) decreased neutrophil oxidative activity synergistically with rolipram (300 nM) in samples stimulated with fMLP and in blood samples primed with TNFα and then stimulated with FMLP.

Production of TNFα by purified human adherent monocytes. A monocyte rich monolayer (>95% monocytes) was prepared by incubating 1 ml of the mononuclear leukocyte fraction ($5 \times 10^5$/ml) from a Ficoll-Hypaque separation in wells of a 24 well tissue culture plate (1 hr; 37° C.; 5% $CO_2$). The non-adherent leukocytes were removed by washing and culture medium added to the wells (1 ml RPMI 1640 containing 1.5 mM HEPES-1% autologous serum with penicillin and streptomycin (250 U/ml and 250 µg/ml, respectively) and ADA (1 U/ml) ±WRC-0470 (30–100 nM), ±endotoxin (10 ng/ml), ±rolipram (300 nM) and ±the adenosine $A_{2A}$ selective antagonist 4-(2-[7-amino-2-(2-furyl)[1,2,4]-triazolo[2,3a]-[1,3,5]trazinyl-amino]ethyl)-phenol (ZM241385) (50 nM). The samples were incubated for 4 hr (37° C.; 5% $CO_2$) and the supernatants harvested. Any suspended cells were removed by centrifugation and the cell-free samples frozen (−70° C.). TNFα was assayed in the cell-free supernatants by an ELISA kit (Cistron Biotechnology, Pine Brook, N.J.).

Figure 7A:
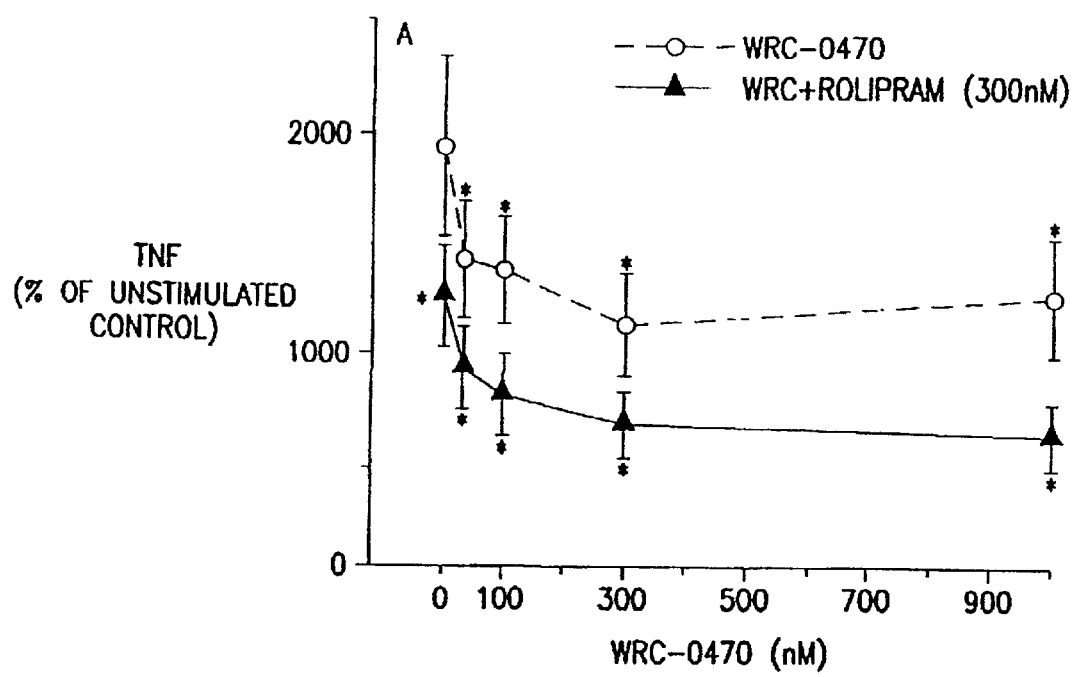
FIG. 7 illustrates the effects of WRC-0470 and Rolipram on the release of TNFα from adherent human monocytes and that this activity is dependent on binding of the adenosine agonist to $A_{2A}$ adenosine receptors.
Figure 7B:
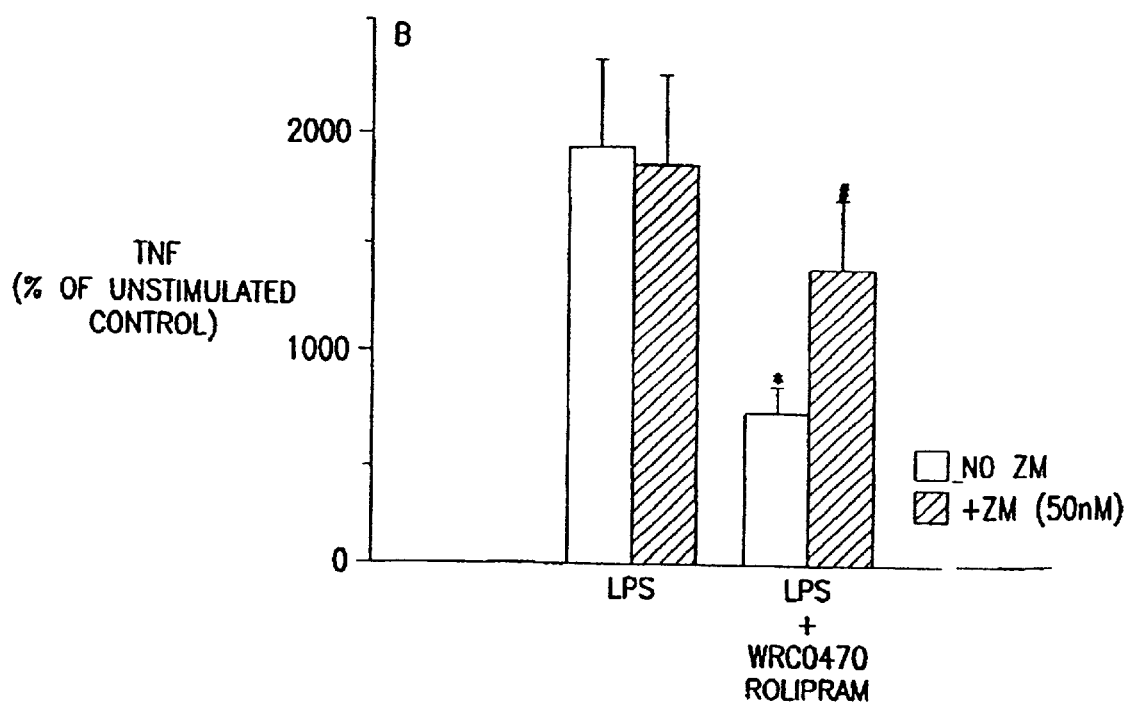

As shown in FIGS. 7A and 7B, WRC-0470 ±rolipram decreased endotoxin-stimulated adherent monocyte production of TNFα ($P<0.050$). As illustrated in FIG. 7B, the $A_{2A}$ selective antagonist ZM241385 significantly inhibited the effect of WRC-0470 (300 nM) combined with rolipram (300 nM) (p=0.020) on TNFα release from monocytes. Hence, WRC-0470 affects TNFα-stimulated neutrophil activity and decreases endotoxin-stimulated TNFα production by monocytes.

Effects of WRC-0470 and rolipram on the extravasation of white blood cells in a rat model of inflammation. Adult wistar rats (approximately 200 g) were anesthetized with intermuscular injections of ketamine and xylazine. Bacteria meningitis (BM) was introduced via intracistemal inoculation of either *E. coli* strain O26:B6LPS (200 ng), cytokines (IL-1 and TNFα or LPS plus cytokines). The animals were then infused with rolipram and/or WRC-1470 over the duration of the experiment using a Harvard pump. CSF (cerebrospinal fluid) and blood was then sampled at 4 h post-inoculation and alterations in BBBP (blood-brain barrier permeability) and WBC (white blood cell) counts were determined. CSF and WBC concentrations were determined with standard hemacytometer methods. For assessment of % BBBP, rats were given an intravenous injection of 5 µCi 125I-labeled bovine serum albumin concomitant with intracistemal inoculation. Equal samples of CSF and blood were read simultaneously in a gamma counter and after subtraction of background radioactivity, % BBBP was calculated by the following formula: % BBBP=(cpm CSF/cpm blood)×100. All statistical tests were performed using Instat biostatistical software to compare the post-inoculation samples of experimental rats with the control rats. The statistical tests used to generate p-values were Student's t-test and ANOVA.

Figure 8:
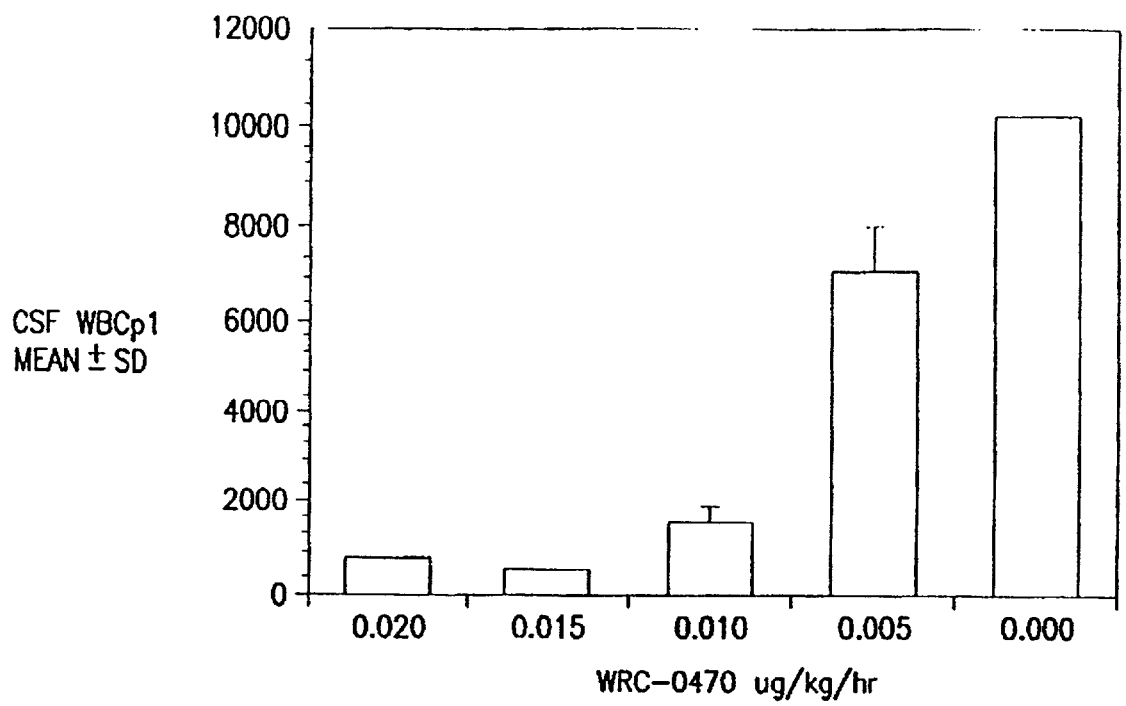
FIG. 8 illustrates the effect of WRC-0470 on white blood cell pleocytosis in rats.
Figure 9:
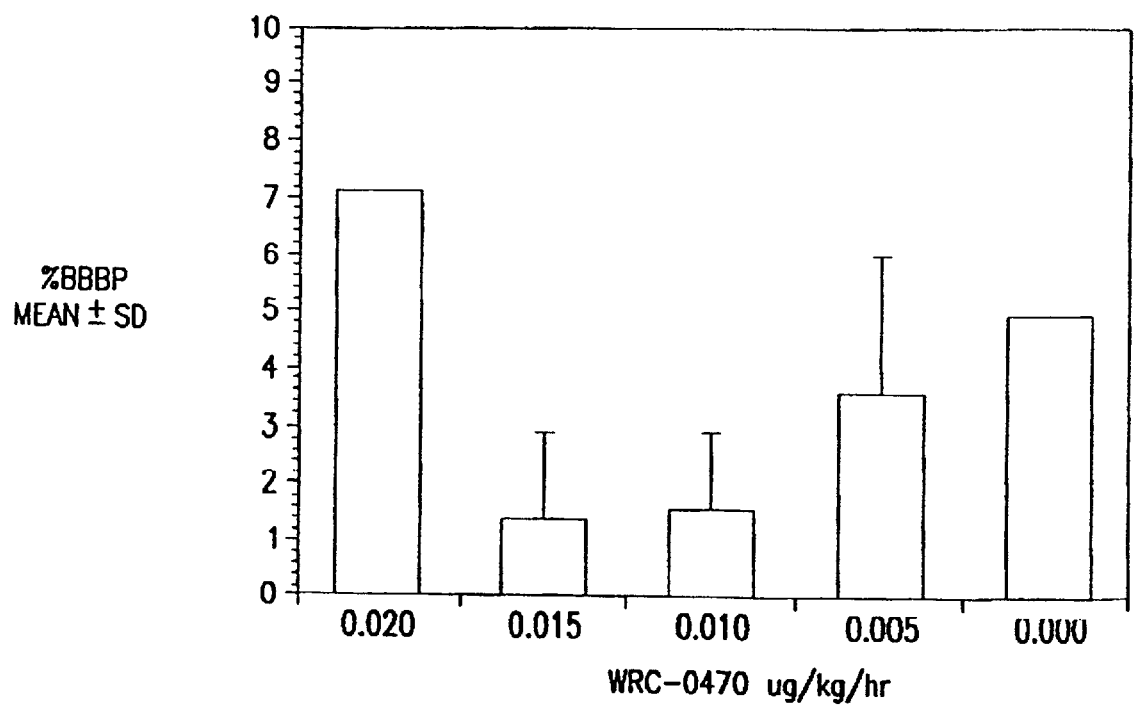
FIG. 9 illustrates the effect of WRC-0470 on blood-brain-barrier permeability in rats.
Figure 10:
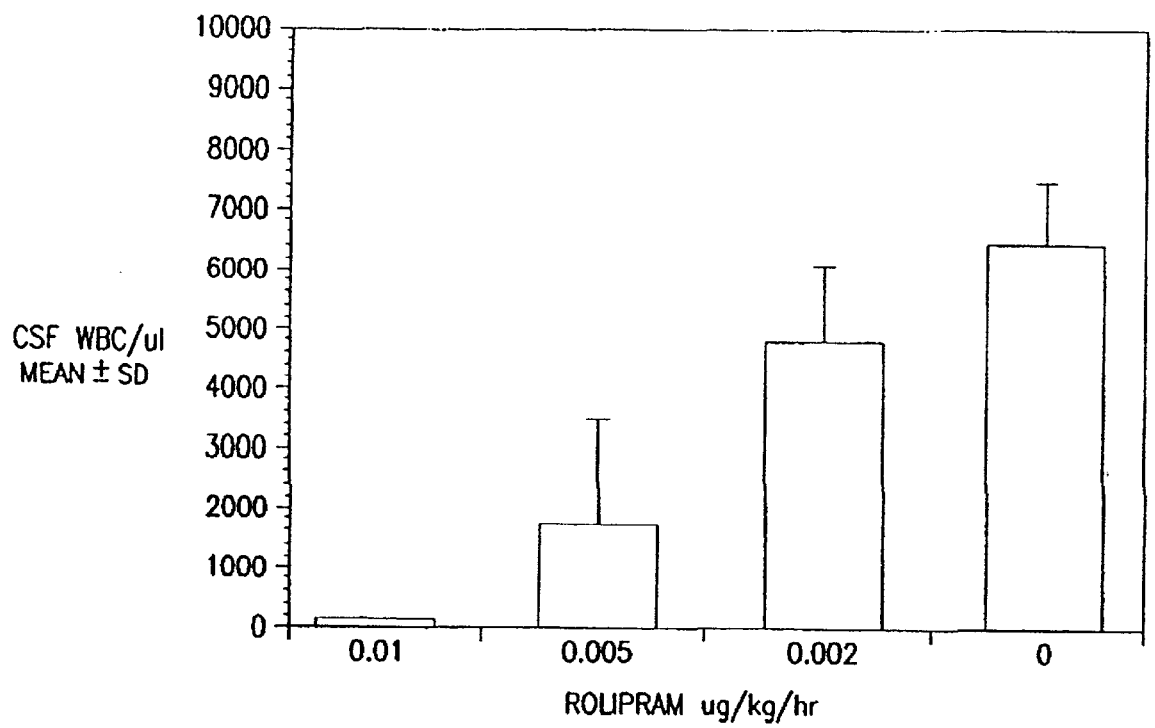
FIG. 10 illustrates the effect of Rolipram on white blood cell pleocytosis in rats.

Results of the tests are reported in FIGS. 8 and 9. Infusion of WRC-0470 at a rate of 0.005–1.2 µg/kg/hr inhibited pleocytosis (p<0.05 as compared to control). The effect of WRC-0470 on BBBP is shown in FIG. 9. A significant response is seen with a range of 0.01–0.015 µg/kg/hr (p<0.05 as compared to control). A rebound effect is noted with the administration of 1.2 µg/kg/hr where % BBBP returned to control. FIG. 10 shows the effect of rolipram on CSF pleocytosis in a range of 0–0.01 µg/kg/hr with 0.01 µg/kg/hr inhibiting 99% of the pleocytosis (p<0.05). Rolipram at either 0.01 or 0.005 µg/kg/hr showed significant inhibition of alterations of BBBP (p<0.05), while a dose of 0.002 µg/kg/hr had no significant effect.

Figure 11:
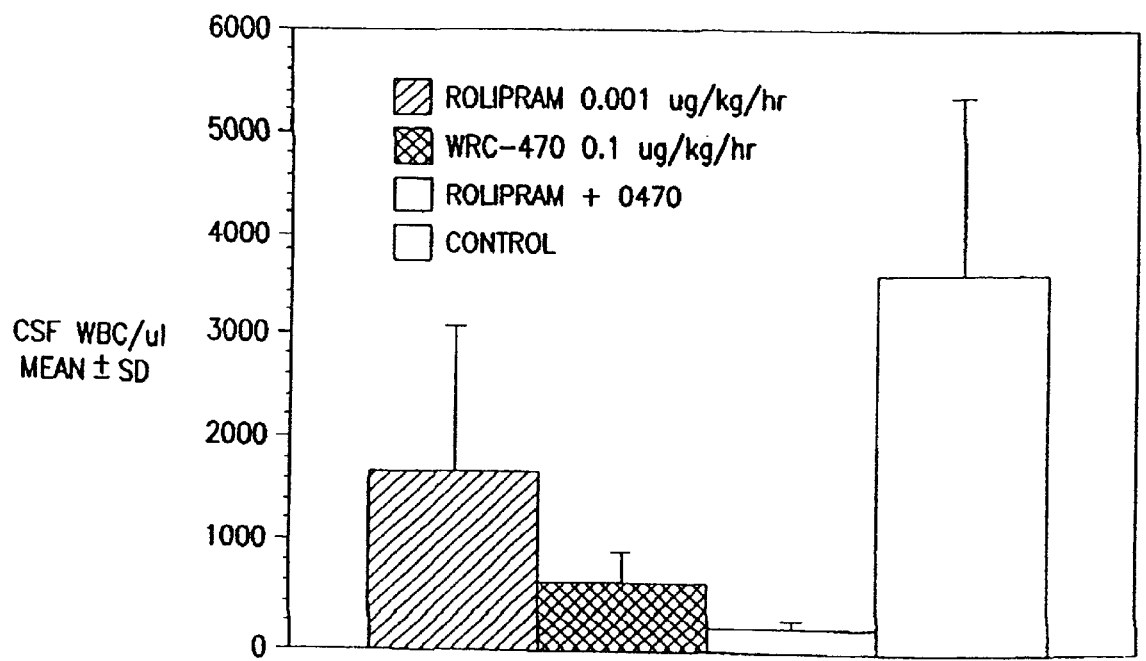
FIG. 11 illustrates the combined effect of WRC-0470 and Rolipram on white blood cell pleocytosis in rats.

The effect of a combination of rolipram and WRC-0470 on CSF WBC pleocytosis is illustrated in FIG. 11. Rolipram (0.001 µg/kg/hr) in combination with WRC-0470 (0.1 µg/kg/hr) inhibited migration of WBC's (200±70 WBC/µl) into the sub-arachnoid space (SAS) to a greater extent than did either rolipram (1,670±1,273 WBC/µl, p<0.050) or WRC-0470 (600±308 WVBCs/µl, p<0.050) alone. The data show a powerful inhibiting effect of WRC-0470 and a synergy with rolipram to prevent inflammation in an animal model.

Application of $A_{2A}$ adenosine receptors with or without rolipram on balloon angioplasty and gene therapy. Balloon angioplasty is commonly used to treat coronary artery stenosis. Restenosis following balloon angioplasty (BA) occurs in up to 40% of coronary interventions. Holmes et al., *American Journal of Cardiology*, 53, 77C-81C (1984). (40%). Restenosis results from a complex interaction of biologic processes, including (I) formation of platelet-rich thrombus; (ii) release of vasoactive and mitogenic factors causing migration and proliferation of smooth muscle cells (SMC); (iii) macrophage and other inflammatory cell accumulation and foam cell (FC) formation; (iv) production of extracellular matrix; and (v) geometric remodeling. Recently the use of coronary stents and pharmacologic intervention using a chimeric antibody to block the integrin on platelets have been partially successful in limiting restenosis after percutaneous coronary interventions in man. Topol et al., *Lencet,* 343, 881–886 (1994). Since inflammatory cell infiltration might be central to the response to injury, and restenotic process, and adenosine, activating via $A_{2A}$ adenosine receptors, inhibits tissues inflammatory cell accumulation, we hypothesize that agonists of $A_2A$ adenosine receptors±Type IV PDE inhibitors will reduce the incidence of restenosis following balloon angioplasty.

In addition, recent advances in local delivery catheters and gene delivery techniques raise the interesting and exciting possibility of administering genes locally into the vessel wall. Nabel et al., *Science,* 249, 1285–1288 (1990); Leclerc et al., *Journal of Clinical Investigation,* 90, 936–944 (1992). Adenoviral-mediated gene transfer affords several advantages over other techniques. However, gene expression is only transient, and has been observed for 7–14 days with diminution or loss of expression by 28 days. Lack of persistence may result from host immune cytolytic responses directed against infected cells. The inflammatory response generated by the present generation of adenovirus results in neointimal lesion formation and may thus offset the benefit of a therapeutic gene. Newman et al., *Journal of Clinical Investigation,* 96, 2955–2965 (1995). An $A_{2A}$ adenosine receptor agonist±a Type IV phosphodiesterase inhibitor in combination with adenovirus may improve the efficiency of gene transfer.

Figure 12:
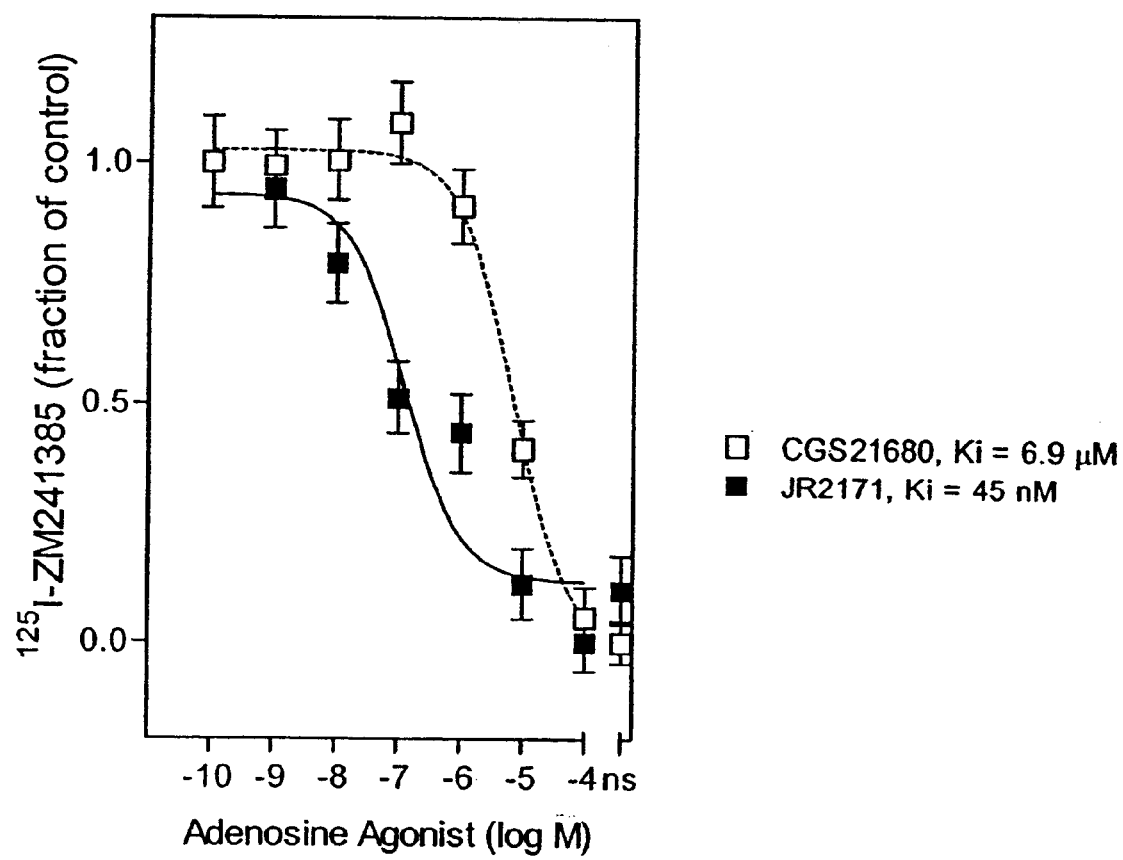
FIG. 12 illustrates the results of a radioligand binding assay in which compounds of the invention CGS21680 and JR2171 were used to compete for the binding of the radioligand, $^{125}$I-ZM241385.

Binding Study of Compounds CGS21680 and JR2171. The results of a radioligand binding assay using CGS21680 and JR2171 to compete for the binding of the radioligand, $^{125}$I-ZM241385, to recombinant human A2A adenosine receptors, is shown in FIG. 12. Based on these binding curves the calculated dissociation constants (Ki values) are on the graph. The Ki of CGS21680 is 6.9 µM (6.9 micromolar), and the Ki of JR2171 is 45 nM (45 nanomolar).

$A_{2A}$ agonists blocking of neutrophil oxidative activity. The adenosine $A_{2A}$ receptor agonist ester (JR2171) to its acid metabolite (CGS21680) were shown to decrease human neutrophil release of pro-inflammatory oxidative products induced by TNF/f-met-leu-phe stimulation. This was detected by luminol-enhanced chemiluminescence. The EC50's were lower for the ester when compared to its acid.

EC50's (M)
JR2171=3.712×10$^{-10}$;
CGS21680=2.086×10$^{-9}$

The unprimed PMN oxidative activity was about 35% of TNF-primed activity

Human Neutrophil Preparation:

A one-step Ficoll-Hypaque separation procedure (Ferrante and Thong, 1980) was used to purify human neutrophils from normal heparinized (10 Units/ml) of venous blood yielding approximately 98% neutrophils; having about >95% viable as determined with trypan blue containing <50 pg/ml of endotoxin. Following separation, the neutrophils were washed with Hank's balanced salt solution (HBSS) three times.

Neutrophil oxidative activity (luminol-enhanced chemiluminescence): The activated neutrophils emit light from unstable high-energy oxygen species produced by the plasma membrane associated NADPH oxidase and metabolized by cytoplasmic and granule enzymes. The light signal from activated neutrophils can be enhanced by the addition of luminol to the samples. The luminol-enhanced emission of light is stimulated by singlet oxygen, a reactive oxygen species, dependent on both the production of superoxide and mobilization of myeloperoxidase from primary granules (DeChatelet et al., 1982).

Figure 13:
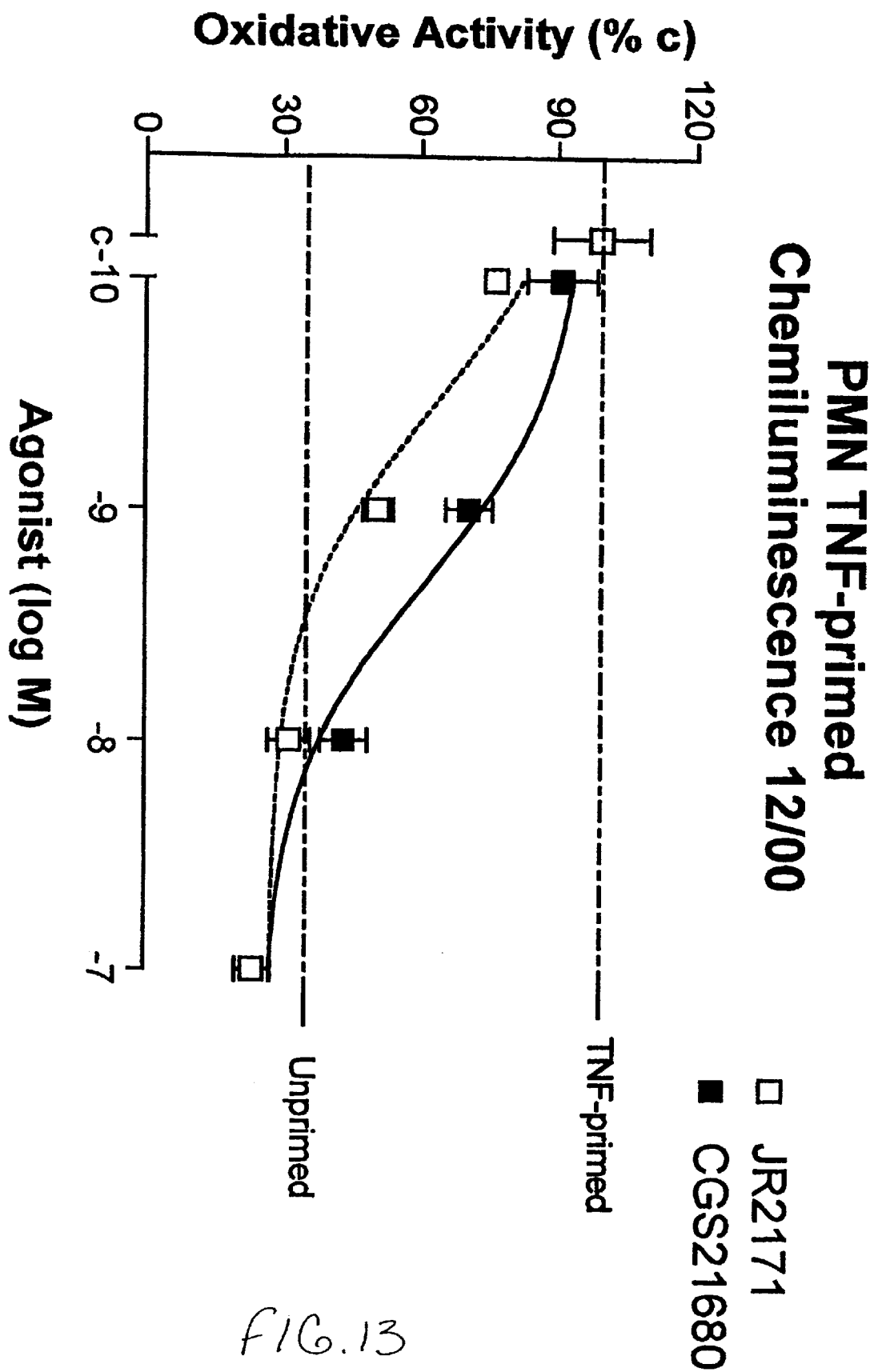
FIG. 13 illustrates the inhibition to a stimulated human neutrophil oxidative burst for compounds CGS21680 and JR2171.

The purified neutrophils (1×10$^6$/ml) were incubated in HBSS containing 0.1% HSA (1 ml), plus adenosine deaminase (1 Units/ml), ±JR2171 or ±CGS21680, and with TNF-alpha (10 U/ml) for 30 min at 37° C. in a shaking water bath. Then luminol (1×10$^4$ M) enhanced f-met-leu-phe (1 µM)-stimulated chemiluminescence was read with a Chronolog Photometer (Chronolog Corp., Havertown, Pa.) at 37° C. for 8 min. Chemiluminescence is reported as relative peak light emitted (=height of the curve) compared to TNFalpha-primed fMLP-stimulated control samples. The results are shown in FIG. 13.

Use of Adenosine $A_{2a}$ Agonists to Prevent Ischemic Injury in the Rabbit Spinal Cord. The spinal cord is sensitive to brief periods of ischemia. When the thoracic aorta is clamped, e.g., during surgery, neurologic impairment can result from a lack of blood flow. A rabbit model for spinal cord ischemia resulting in paraplegia is described below.

A laparotomy is performed on a group of rabbits following general anesthesia. The infrarenal aorta is clamped for about forty-five minutes. Cross-clamping the infrarenal aorta causes spinal cord ischemia. The animals are split into two groups. The first group are administered an $A_{2A}$ adenosine agonist, e.g., WRC-0470, 10 µg/kg, infused over about 3 hours. The infusion is started after about 30 minutes of ischemic time. The second group is not administered the $A_{2A}$ adenosine agonist. The animals are allowed to recover for about 48 hours, and assessed for neurologic impairment using the Tarlov (0–5) scoring system. The animals treated with the $A_{2A}$ agonists of formula (I or VI) exhibit substantially less neurological impairment (0–3) than control (untreated) animals.

All patents, patent applications, books and literature cited in the specification are hereby incorporated by reference in their entirety. In the case of any inconsistencies, the present disclosure, including any definitions therein will prevail. The invention has been described with reference to various specific and preferred embodiments and techniques. However, it should be understood that many variations and modifications may be made while remaining within the spirit and scope of the invention. It is therefore to be understood that, within the scope of the appended claims, the invention may be practiced otherwise than as specifically described herein.

What is claimed:

1. A therapeutic method to inhibit an inflammatory response comprising administering, to a mammal in need of the therapy, an effective anti-inflammatory amount of an agonist of an $A_{2A}$ adenosine receptor of formula (VI):

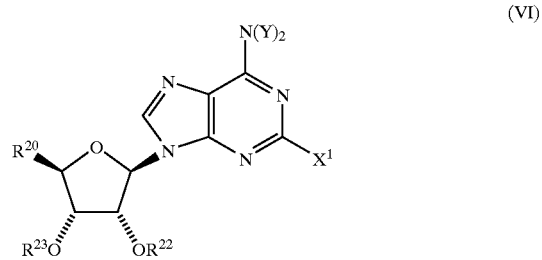

(VI)

wherein
X' is —NR$^{13}$R$^{14}$;
R$^{13}$ is hydrogen or $C_{1-4}$-alkyl; and R$^{14}$ is
$C_{1-4}$-alkyl substituted with one or more $C_{6-10}$-aryl wherein aryl is substituted with one or more R$^{15}$OOC—($C_{1-4}$-alkyl)-, or R$^{16}$R$^{17}$NC(=O)—($C_{1-4}$alkyl)-, and
wherein each Y is individually H, $C_1$–$C_6$ alkyl, $C_{3-7}$-cycloalkyl, phenyl or phenyl $C_{1-3}$ alkyl;

$R^{20}$ is —C(=O)NR$^{16}$R$^{17}$, —COOR$^{15}$, or —CH$_2$OR$^{15}$;
wherein each of R$^{16}$ and R$^{17}$ are independently;
  (a) hydrogen;
  (b) $C_{3-7}$-cycloalkyl;
  (c) $C_{1-4}$-alkyl;
  (d) $C_{1-4}$-alkyl substituted with one or more $C_{1-4}$-alkoxy, halogen, hydroxy, —COOR$^{21}$, amino, mono($C_{1-4}$-alkyl)amino, di($C_{1-4}$-alkyl)amino or $C_{6-10}$-aryl wherein aryl is optionally substituted with one or more halogen, $C_{1-4}$-alkyl, hydroxy, amino, mono($C_{1-4}$-alkyl)amino or di($C_{1-4}$ alkyl)amino;
  (e) $C_{6-10}$-aryl; or
  (f) $C_{6-10}$-aryl substituted with one or more halogen, hydroxy, amino, mono($C_{1-4}$-alkyl)amino, di($C_{1-4}$ alkyl) amino or $C_{1-4}$-alkyl;
$R^{22}$ and $R^{23}$ independently represent hydrogen, lower alkanoyl, lower alkoxy-lower alkanoyl, aroyl, carbamoyl or mono- or di-lower alkylcarbamoyl; and
$R^{15}$ is $C_{1-4}$-alkyl, $C_{6-10}$-aryl or $C_{6-10}$-aryl($C_{1-4}$-alkyl); and $R^{21}$ is hydrogen, independently $C_{1-4}$-alkyl, $C_{6-10}$-aryl or $C_{6-10}$-aryl($C_{1-4}$-alkyl);
or a pharmaceutically acceptable salt thereof.

2. The method of claim 1, further comprising administering the agonist with an effective anti-inflammatory amount of a Type IV phosphodiesterase inhibitor.

3. The method of claim 2, wherein the Type IV phosphodiesterase inhibitor and $A_{2A}$ agonist exhibit a synergistic anti-inflammatory effect.

4. The method of claims 1, or 2, wherein $R^{14}$ is $C_{1-4}$-alkyl substituted with $C_{6-10}$-aryl wherein aryl is substituted with $R^{15}$OOC—($C_{1-4}$-alkyl).

5. The method of claim 4, wherein one of $R^{16}$ and $R^{17}$ is $C_{1-4}$-alkyl substituted with one or more $C_{1-4}$-alkoxy, halogen, hydroxy, amino, mono($C_{1-4}$-alkyl)amino, di($C_{1-4}$-alkyl)amino or $C_{6-10}$-aryl wherein aryl is optionally substituted with one or more halogen, hydroxy, amino, $C_{1-4}$-alkyl, $R^{15}$OOC—($C_{1-4}$-alkyl), mono($C_{1-4}$-alkyl)amino or di($C_{1-4}$-alkyl)amino.

6. The method of claim 4, wherein one of $R^{16}$ and $R^{17}$ $C_{6-10}$-aryl substituted with one or more halogen, hydroxy, amino, mono($C_{1-4}$-alkyl)amino, di($C_{1-4}$ alkyl)amino or $C_{1-4}$-alkyl.

7. The method of claim 4, wherein $R^{16}$ is hydrogen and $R^{17}$ is $C_{1-4}$-alkyl, cyclopropyl or hydroxy-$C_{2-4}$-alkyl.

8. The method of claim 5, wherein $R^{13}$ is hydrogen and $R^{14}$ is $C_{1-4}$-alkylsubstituted with $C_{6-10}$-aryl substituted with $R^{15}$OOC—($C_{1-4}$-alkyl).

9. The method of claims 1 or 2, wherein the compound having formula (VI) is:

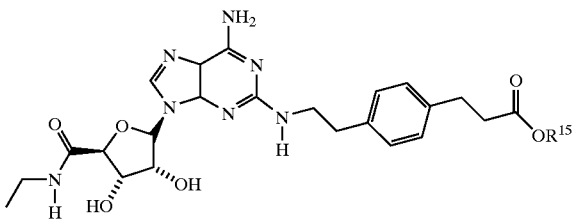

wherein $R^{15}$ is methyl, ethyl, n-propyl, isopropyl or tert-butyl.

10. The method of claim 9, wherein $R^{15}$ is methyl or ethyl.
11. The method of claim 10, wherein $R^{15}$ is methyl.
12. The method of claim 2, wherein said Type IV phosphodiesterase inhibitor is a compound having formula (V):

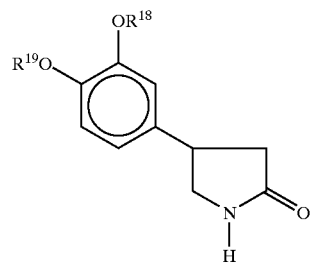

wherein $R^{18}$ and $R^{19}$ each are alike or different and are hydrocarbon radicals having up to 18 carbon atoms with at least one being other than methyl, a heterocyclic ring or alkyl of 1–5 carbon atoms which is substituted by one or more of halogen atoms, hydroxy, carboxy, alkoxy, alkoxycarbonyl or an amino group; or amino.

13. The method of claim 12, wherein said Type IV phosphodiesterase inhibitor is rolipram.

14. The method of claim 13, wherein said agonist of an $A_{2A}$ adenosine receptor is

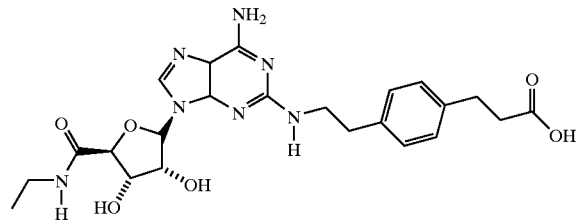

and said Type IV phosphodiesterase inhibitor is rolipram.

15. The method of claim 13, wherein said agonist of an $A_{2A}$ adenosine receptor is

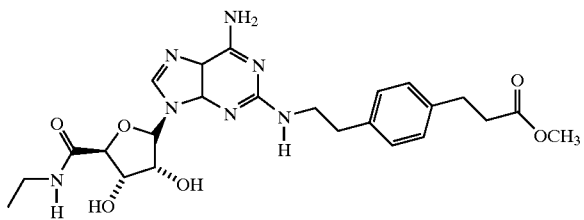

and said Type IV phosphodiesterase inhibitor is rolipram.

16. The method of claim 2, wherein said $A_{2A}$ adenosine receptor agonist and said Type IV phosphodiesterase inhibitor are co-administered to the patient in need thereof.

17. A pharmaceutical composition comprising an effective anti-inflammatory amount of an agonist of an $A_{2A}$ adenosine receptor according to claim 1 in combination with an effective amount of a Type IV phosphodiesterase inhibitor.

18. The composition of claim 17, which is adapted for topical administration.

19. The composition of claim 17, which is adapted for aerosol administration.

20. The method of claims 1 or 2, wherein the $A_{2A}$ agonist is administered topically.

21. The method of claims 1 or 2, wherein the $A_{2A}$ agonist is administered as an aerosol.

* * * * *